United States Patent
Zhang et al.

(10) Patent No.: US 9,606,076 B2
(45) Date of Patent: Mar. 28, 2017

(54) PROCESS FOR EVALUATING CORROSION RESISTANCE OF COATING

(75) Inventors: Shi Hua Zhang, Wilmington, DE (US); Lorenzo Fred Pelosi, Wilmington, DE (US); Robert C. Nahas, Voorhees, NJ (US)

(73) Assignee: AXALTA COATING SYSTEMS IP CO., LLC, Wilmington, DE (US)

( * ) Notice: Subject to any disclaimer, the term of this patent is extended or adjusted under 35 U.S.C. 154(b) by 900 days.

(21) Appl. No.: 13/996,576

(22) PCT Filed: Dec. 21, 2011

(86) PCT No.: PCT/US2011/066453
§ 371 (c)(1),
(2), (4) Date: Aug. 22, 2013

(87) PCT Pub. No.: WO2012/088256
PCT Pub. Date: Jun. 28, 2012

(65) Prior Publication Data
US 2013/0325364 A1    Dec. 5, 2013

Related U.S. Application Data

(60) Provisional application No. 61/425,458, filed on Dec. 21, 2010.

(51) Int. Cl.
*G01N 27/02* (2006.01)
*G01N 17/02* (2006.01)

(52) U.S. Cl.
CPC .............. *G01N 27/02* (2013.01); *G01N 17/02* (2013.01)

(58) Field of Classification Search
CPC ...... G01N 27/02; G01N 17/02; G01N 21/359; G01N 27/00; G06Q 10/06
See application file for complete search history.

(56) References Cited

U.S. PATENT DOCUMENTS 6,383,451 B1    5/2002  Kim et al.
2004/0061510 A1    4/2004  Hands
(Continued)

FOREIGN PATENT DOCUMENTS

CN    1570591 A    1/2005
CN    101634623 A    1/2010
(Continued)

OTHER PUBLICATIONS

ISA KIPO, International Search Report for Application No. PCT/US2011/066453, dated Jun. 19, 2012.
(Continued)

*Primary Examiner* — Mohamed Charioui
*Assistant Examiner* — Jeremy Delozier
(74) *Attorney, Agent, or Firm* — Lorenz & Kopf LLP

(57) ABSTRACT

The present invention is directed to a process for evaluating corrosion resistance of coated metals substrates, such as autobodies at accelerated rate. An anode and cathode coated with protective coating being tested are exposed to an electrolyte in a chamber of a corrosion resistance evaluator. These coatings are provided with predetermined and standardized defects, such as micro-holes to accelerate the corrosion of the underlying metal substrate in a predictable and repeatable manner. The coated cathode/anode pair is subject to a start-up period followed by series preset DC voltages modulated in a stepwise manner for preset durations that are interspaced with recovery periods. The impedance data collected are then used to arrive at the corrosion performance resistance of the coating applied over the cathode/anode pair. The foregoing evaluator substantially reduces the time required to test corrosion from several days (40 plus days) to few days (about two days).

17 Claims, 17 Drawing Sheets

(56) References Cited

U.S. PATENT DOCUMENTS

2006/0002815 A1    1/2006  Harris et al.
2012/0095698 A1*   4/2012  Zhang .................... G01N 17/02
                                                        702/30

FOREIGN PATENT DOCUMENTS

WO      2010078547 A1    7/2010
WO      2010078548 A1    7/2010

OTHER PUBLICATIONS

ISA KIPO, International Preliminary Report on Patentability for Application No. PCT/US2011/066453, dated Jul. 4, 2013.
SIPO, Chinese Office Action for Application No. 201180068171.2, dated Nov. 26, 2014.

* cited by examiner

Continued from Fig. 4A

> Means for configuring computer readable program code devices to cause said computer to determine start-up resistances ($^{Sta}R_{Sta.nl}$) by:
>
> 1. measuring a distance between zero point on X-axis of said A impedance Nyquist plot and a point on said X-axis of said A impedance Nyquist plot where an impedance curve or an extrapolated impedance curve directed to low start-up resistance frequencies in said A impedance Nyquist plot intersects said X-axis to obtain real part of said impedance A at said low start-up resistance frequencies; and
>
> 2. repeating said step (1) for each said impedance A in said n1 set;

—416

> Means for configuring computer readable program code devices to cause said computer to direct said direct current variable power generator to apply V1 preset DC voltages in a stepwise manner for T1 preset durations, wherein said direct current measurement device in communication with said computer and connected to said cathode and said anode is used to measure said preset DC voltages and wherein said V1 preset DC voltage ranges from 0.1 millivolts to 10 volts and said T1 preset duration ranges from half an hour to 100 hours;

—418

> Means for configuring computer readable program code devices to cause said computer to direct said impedance measurement device to measure an impedance B at the end of each of said preset duration at said preset frequencies of AC power supplied by said alternating current variable power generator to produce n2 set of said impedances B;

Continued from Fig. 4D

Means for configuring computer readable program code devices to cause said computer to determine recovery resistances ($^{Rec}R_{Rec.n3}$) by:

1. measuring a distance between zero point on X-axis of said C impedance Nyquist plot and a point on said X-axis of said C impedance Nyquist plot where an impedance curve or an extrapolated impedance curve directed to low recovery resistance frequencies in said C impedance Nyquist plot intersects said X-axis to obtain real part of said impedance C at said low recovery resistance frequencies; and 2. repeating said step (1) for each said impedance C in said n3 set; — 432

Means for configuring computer readable program code devices to cause said computer to calculate corrosion performance resistance ($R_{perf}$) of said anode and said cathode pair by using the following equation:

$$R_{perf} = \left[\sum Sta_{f_{n1}}(^{Sta}R_{Sta.n1} - {}^{Sta}R_{Sol.n1})\right]/n1 +$$
$$\left[\sum Stp_{f_{n2}}(^{Stp}R_{Stp.n2} - {}^{Stp}R_{Sol.n2})\right]/n2 +$$
$$\left[\sum Rec_{f_{n3}}(^{Rec}R_{Rec.n3} - {}^{Rec}R_{Sol.n3})\right]/n3, \text{ wherein}$$

n1, n2, n3 and n3 range from 1 to 100; and $Sta_{f_{n1}}$, $Stp_{f_{n2}}$, and $Rec_{f_{n3}}$ range from 0.0000001 to 1; and — 434

Continued from Fig. 4E

Means for configuring computer readable program code devices to cause said computer to:

(q1) direct a computer monitor to display said corrosion performance resistance ($R_{perf}$);

(q2) direct a printer to print said corrosion performance resistance ($R_{perf}$);

(q3) transfer said corrosion performance resistance ($R_{perf}$) to a remote computer or a remote database; or (q4) a combination thereof

PROCESS FOR EVALUATING CORROSION RESISTANCE OF COATING

CROSS-REFERENCE TO RELATED APPLICATION

This application is a U.S. National-Stage entry under 35 U.S.C. §371 based on International Application No. PCT/US2011/066453, filed Dec. 21, 2011 which was published under PCT Article 21(2) and which claims priority to U.S. Provisional Application No. 61/425,458, filed Dec. 21, 2010, which are all hereby incorporated in their entirety by reference.

FIELD OF INVENTION

The present invention is directed to a process for evaluating the corrosion resistance of multi-coated and single coated metal substrates and more particularly directed to a corrosion resistance evaluator and to a process used therein for evaluating the corrosion resistance of multi-coated and single coated metal substrates at an accelerated rate.

BACKGROUND OF INVENTION

Currently, no short term (less than 2 days) test method exists to evaluate the long-term corrosion protection afforded by a protective coating from a coating composition, such as automotive OEM or automotive refinish coating compositions, applied over a metal substrate, such as automotive body. The current standard test methods rely primarily on environmental chamber exposure, followed by visual and mechanical testing of the metal with its protective coating. This kind of testing is long (up to 40 days or more exposure time), subjective, highly dependent on the exposure geometry, and on the person doing the evaluation. Consequently, these methods are not very reproducible. The corrosion resistance data is qualitative, and therefore the relative performance of an acceptable coating cannot be easily determined. Any new test method must correlate well with the traditional, the accepted, standard environmental chamber test methods, must be reproducible, and must supply a qualitative and quantitative ranking of the unknown direct-to-metal (DTM) corrosion resistant coating.

The experimental corrosion test methods have been reported for reducing the test duration. These methods primarily utilize electrochemical impedance spectroscopy (EIS) or AC impedance technology. Since these AC impedance based methods typically only offer a more sensitive tool for detecting corrosion at an early stage of exposure time, the corrosion process itself is not accelerated by these methods. Therefore, these methods still require relatively long exposure times before the meaningful data can be obtained. The length of time needed to get meaningful corrosion data approaches that of the standard methods. More importantly, the corrosion resistance data obtained by these methods, particularly during the initial exposure time, are primarily dictated by the intrinsic defects of the coatings. These intrinsic defects generally produced during the preparation of coated samples are not necessarily related to the actual performance of the coatings. Misleading information could be obtained if the data are not analyzed correctly. Consequently, the standard convention methods are still favored. Therefore, a need still exists for a device and a process that not only accelerates the corrosion of protectively coated metal substrates but also mimics the corrosion typically seen in working environments, such as those experienced by bodies of automobiles during use.

STATEMENT OF INVENTION

The present invention is directed to a process for evaluating corrosion resistance of an anode coating applied over a surface of an anode and corrosion resistance of a cathode coating applied over a surface of a cathode comprising:

(i) sealably positioning said anode in an anode holder located on a chamber of a corrosion resistance evaluator, said chamber containing an electrolyte therein such that a portion of said anode coating is exposed to said electrolyte, said portion of said anode coating having an anode defect thereon;

(ii) sealably positioning said cathode in a cathode holder located on said chamber such that a portion of said cathode coating is exposed to said electrolyte, said portion of said cathode coating having a cathode defect thereon;

(iii) directing a computer of said evaluator through computer readable program code means residing on a usable storage medium located in said computer and configured to cause said computer to perform following steps comprising:

a) subjecting said portions of said anode coating and said cathode coating to a start-up period;

b) directing an impedance measurement device in communication with said computer and is connected to said cathode and said anode to measure an impedance A during said start-up period at preset intervals to produce n1 set of said impedances A measured at preset frequencies ranging from 100000 to $10^{-6}$ Hz of AC power with an amplitude ranging from 10 to 50 mV supplied by an alternating current variable power generator in communication with said computer, said alternating current variable power generator having AC output leads that connect to said cathode and anode;

c) generating A impedance Nyquist plot for each said impedance A in said n1 set;

d) determining start-up solution resistances ($^{Sta}R_{sol.n1}$) by:
 1. measuring a distance between zero point on X-axis of said A impedance Nyquist plot and a point on said X-axis of said A impedance Nyquist plot where an impedance curve or an extrapolated impedance curve directed to high start-up solution frequencies in said A impedance Nyquist plot intersects said X-axis to obtain real part of said impedance A at said high start-up solution frequencies; and
 2. repeating said step (d) (1) for each said impedance A in said n1 set;

e) determining start-up resistances ($^{Sta}R_{Sta.n1}$) by:
 1. measuring a distance between zero point on X-axis of said A impedance Nyquist plot and a point on said X-axis of said A impedance Nyquist plot where an impedance curve or an extrapolated impedance curve directed to low start-up resistance frequencies in said A impedance Nyquist plot intersects said X-axis to obtain real part of said impedance A at said low start-up resistance frequencies; and
 2. repeating said step (e) (1) for each said impedance A in said n1 set;

f) directing a direct current variable power generator to apply V1 preset DC voltages in a stepwise manner for T1 preset durations, wherein said direct current measurement device in communication with said computer and connected to said cathode and said anode is used to measure said preset DC voltages and wherein said V1 preset DC voltage ranges from 0.1 millivolts to 10 volts and said T1 preset duration ranges from half an hour to 100 hours;

g) directing said impedance measurement device to measure an impedance B at the end of each of said preset duration at said preset frequencies of AC power supplied by said alternating current variable power generator to produce n2 set of said impedances B;

h) generating B impedance Nyquist plot for each said impedance B in said n2 set;

i) determining stepped-up solution resistances ($^{Stp}R_{sol.n2}$) by:
  1. measuring a distance between zero point on X-axis of said B impedance Nyquist plot and a point on said X-axis of said B impedance Nyquist plot where an impedance curve or an extrapolated impedance curve directed to high stepped-up solution frequencies in said B impedance Nyquist plot intersects said X-axis to obtain real part of said impedance B at said high stepped-up solution frequencies;
  2. repeating said step (i) (1) for each said impedance B in said n2 set;

j) determining stepped-up resistances ($^{Stp}R_{Stp.n2}$) by:
  1. measuring a distance between zero point on X-axis of said B impedance Nyquist plot and a point on said X-axis of said B impedance Nyquist plot where an impedance curve or an extrapolated impedance curve directed to low stepped-up resistance frequencies in said B impedance Nyquist plot intersects said X-axis to obtain real part of said impedance B at said low stepped-up resistance frequencies; and
  2. repeating said step (j) (1) for each said impedance B in said n2 set;

k) subjecting said portions of said anode coating and said cathode coating to T2 preset recovery periods in between each of said T1 preset durations;

l) directing said impedance measurement device to measure an impedance C at the end of each of said T2 preset recovery periods at said preset frequencies of AC power supplied by said alternating current variable power generator to produce n3 set of said impedances C;

m) generating C impedance Nyquist plot for each said impedance C in said n3 set;

n) determining recovery solution resistances ($^{Rec}R_{sol.n3}$) by:
  1. measuring a distance between zero point on X-axis of said C impedance Nyquist plot and a point on said X-axis of said C impedance Nyquist plot where an impedance curve or an extrapolated impedance curve directed to high recovery solution frequencies in said C impedance Nyquist plot intersects said X-axis to obtain real part of said impedance C at said high recovery solution frequencies;
  2. repeating said step (n) (1) for each said impedance C in said n3 set;

o) determining recovery resistances ($^{Rec}R_{Rec.n3}$) by
  1. measuring a distance between zero point on X-axis of said C impedance Nyquist plot and a point on said X-axis of said C impedance Nyquist plot where an impedance curve or an extrapolated impedance curve directed to low recovery resistance frequencies in said C impedance Nyquist plot intersects said X-axis to obtain real part of said impedance C at said low recovery resistance frequencies; and
  2. repeating said step (o) (1) for each said impedance C in said n3 set;

p) calculating corrosion performance resistance ($R_{perf}$) of said anode and said cathode pair by using the following equation:

$$R_{perf} = [\Sigma^{Sta}f_{n1}(^{Sta}R_{Sta.n1} - ^{Sta}R_{Sol.n1})]/n1 + [\Sigma^{Stp}f_{n2}(^{Stp}R_{Stp.n2} - ^{Stp}R_{Sol.n2})]/n2 + [\Sigma^{Rec}f_{n3}(^{Rec}R_{Rec.n3} - ^{Rec}R_{Sol.n3})]/n3,$$

wherein n1, n2, n3 and n3 range from 1 to 100; and $^{Sta}f_{n1}$, $^{Stp}f_{n2}$, and $^{Rec}f_{n2}$ range from 0.0000001 to 1; and q) causing computer 40 to direct a computer monitor 52 to:
  (q1) display the corrosion performance resistance ($R_{perf}$),
  (q2) direct a printer 54 to print the corrosion performance resistance ($R_{perf}$),
  (q3) transfer the corrosion performance resistance ($R_{perf}$) to a remote computer 56 or a remote database, or
  (q4) a combination thereof.

BRIEF DESCRIPTION OF DRAWING

FIGS. 4A, 4B, 4C, 4D, 4E and 4F represent a flowchart of means for configuring computer readable program code means used in the device of the present invention illustrated in FIG. 3.

DETAILED DESCRIPTION OF PREFERRED THE EMBODIMENT

Figure 1:
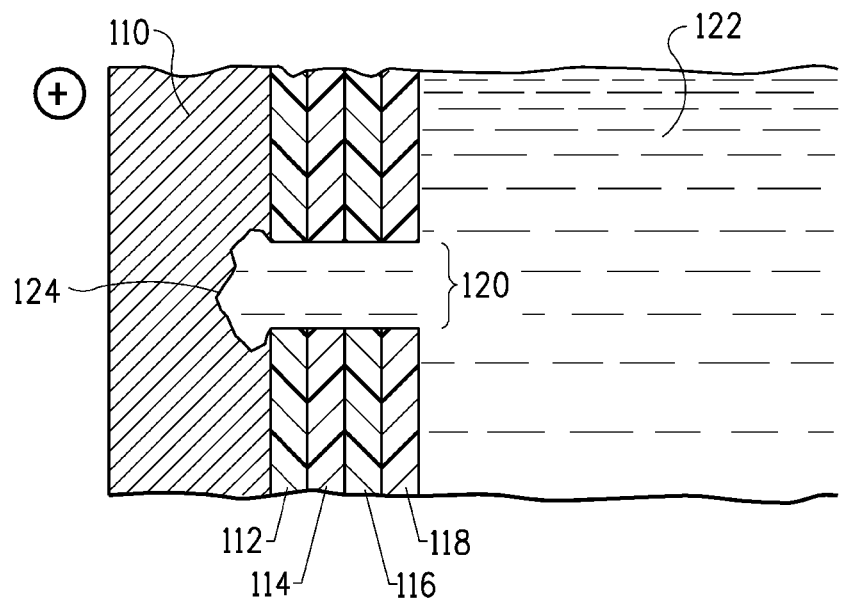
FIG. 1 broadly illustrates the process of anodic metal dissolution that occurs at anode.

The evaluation of corrosion resistance of single layer or multilayer protective coatings, such as those resulting from an automotive OEM paint, an automotive refinish paint, a marine paint, an aircraft paint, an architectural paint, an industrial paint, a rubberized coating, a polytetrafluoroethylene coating, or a zinc-rich primer, typically applied over metal substrates, such as steel, aluminum and copper, is very important for determining the working life of a product, such as an automobile, a ship or a crane.

When a metal substrate, such as an automobile body, is exposed to atmosphere, its surface is covered by a thin film of water produced by the condensation of moisture in air, although it may not be visible due to the extremely low thickness of the film. Many micro electrochemical corrosion cells can develop on the surface of metal substrate underneath the water film due to the non-uniform properties of the metal substrate. Such non-uniformity can result from the differences in chemical composition of the metal, differences in metal microstructure, or due to the differences in mechanical stress of the surface of a metal. Such non-uniformity can lead to the formation of electrode potential difference on the surface. It is believed that when the surface of metal is covered by the electrolyte, such as water formed by the condensation of moisture, the locations with a lower electrode potential turn into an anode while the locations with a higher electrode potential turn into a cathode. These anodes and cathodes, covered with the electrolyte, can form many micro electrochemical corrosion cells across over the entire surface of metal, which in turn can produce corrosion. A workable corrosion cell is generally composed of three sub-processes—an anodic process, a cathodic process, and an electrolyte pathway to transfer ionic species. The anode process in the corrosion is the metal that loses electrons to form its ionic species and thus can be dissolved into the electrolyte as illustrated in the following manner:

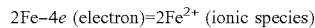

$$2Fe - 4e \text{ (electron)} = 2Fe^{2+} \text{ (ionic species)} \qquad 1$$

When the condition is neutral, the cathode process in the corrosion is the reduction of oxygen which gains the electrons released from the anode in the following manner:

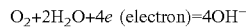

$$O_2 + 2H_2O + 4e \text{ (electron)} = 4OH^- \qquad 2$$

This oxygen, required by the cathode process, generally comes from the oxygen dissolved in the water. In the electrolyte, such as water, $Fe^{2+}$ released from the anode transports towards cathode, and at the same time, $OH^-$ produced on the cathode transports toward anode. Eventually, they neutralize each other to keep the electrolyte at a neutral condition. For a workable micro corrosion cell, the anode and cathode process have to occur at the same time. The corrosion stops whenever either of them is eliminated. For the corrosion of coated systems, a similar corrosion mechanism occurs, but with some special features described below.

Due to the coverage of metal surface by coating, it takes a long time for the water to permeate through the coating thickness to approach the interface of coating/metal substrate. Corrosion occurs only when the water approaches the metal surface, or more specifically, the interface of coating/metal substrate. However, if the coating has defects, such as micro-cracks, corrosion can be initiated immediately inside these defects. As a result, the corrosion data obtained by a conventional AC impedance evaluation method, dictated or distorted by the intrinsic defects of the coating, may not represent the actual true performance of the coating. As noted by the cathode reaction (in Equation 2 above), the pH of the cathode area is increased significantly when corrosion occurs. For many coating formulations, such an increased pH promotes delamination of coating film from the metal substrate, which is one of the primary coating failure modes.

Under working conditions, these micro-anodes and micro-cathodes are randomly distributed across the entire surface of metal substrate and they are not distinguishable. However, in the device and process of present invention, the anode and cathode are separated so that these anodic and cathodic processes can be controlled and accelerated individually.

The preferred embodiment of this invention provide for:

An AC impedance method suitable for sensitively detecting any change caused by the corrosion of metal substrate under the coating film;

A cathode separated from an anode in the device and process allows one to respectively separately control and accelerate the corrosion process occurring on the cathode and anode;

Artificial defects are provided on the anode and cathode so that the effect of the intrinsic defects can be eliminated.

The present invention provides for a device and a process for comprehensively evaluating the performance of coatings under various controlled and accelerated conditions. In the start up period, the performance of the coatings is evaluated under a natural condition. In the stepped-up period, the performance of the coatings is evaluated at an accelerated condition. In this period, the anodic corrosion process at the anode site and the delamination process on the cathode site are accelerated separately and gradually by means of sequentially stepped DC voltages applied across the cathode and anode. The inhibitive effect at the anode site, and the delamination resistance on the cathode site are evaluated at the same time. In the recovery period, the recovery performances of the coatings are evaluated after stopping the severe corrosion that occurs when stepped DC voltages are applied across the cathode and anode.

Figure 2:
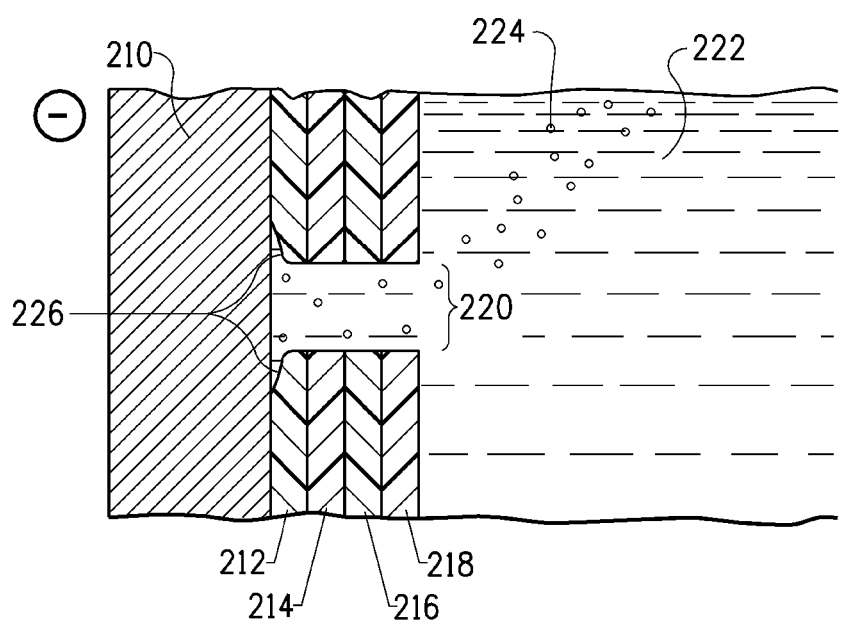
FIG. 2 broadly illustrates the process of delamination that occurs at cathode.

FIGS. 1 and 2 illustrate the typical anodic dissolution process that occurs at an anode (FIG. 1) and the delamination processes that occur at a cathode (FIG. 2) of the present invention.

FIG. 1 illustrates the anodic end of the device of the present invention of a typical multi-coating system applied over a metal substrate 110, FIG. 1 includes a dry conversion coating layer (phosphate layer) 112 typically ranging in thickness from 2 to 50 nanometers applied over a metal substrate 110, followed by a dry layer of an electro-coated primer 114 typically ranging in thickness from 25 to 250 micrometers, then followed by a dry layer of either a basecoating or a sealer-basecoating combination 116 typically ranging in thickness from 20 to 50 micrometers for the sealer, and 50 micrometers to 120 micrometers for the basecoating (color coating). Typically, basecoating 116 is protected with a dry layer of a clearcoating 118 ranging in thickness from 30 micrometers to 100 micrometers. A standardized defect is represented by a defect 120 that exposes metal substrate 110 to an electrolyte 122, such as 3% sodium chloride containing dissolved oxygen. If the metal substrate 110 is a cold rolled steel, ferrous ions are released in the electrolyte and over time, the surface of substrate 110 corrodes to form pits 124, rust scales etc. Then the size of defect 120 may be increased over time by corrosion, which then separates the multi-coating from metal substrate 110 and corrodes and damages the underlying surface.

FIG. 2 illustrates the cathodic end of the device of the present invention. FIG. 2 shows a typical multi-coating applied over an automobile metal body 210, which includes a dry layer of a conversion coating 212 applied over metal substrate 210, followed by a dry layer of an electro-coated primer 214 followed by a dry layer of a basecoating 216 followed by a dry layer of a clearcoating 218, all having thicknesses mentioned in the paragraph above. A standardized defect is represented by a defect 220 that exposes metal substrate 210 to an electrolyte 222, such as 3% sodium chloride containing dissolved oxygen. When cathodic reactions occur, driven by the DC voltages applied, it is believed the pH at the cathode site will be increased due to the reduction of oxygen, and a higher pH will promote the delamination of the multi-coating from metal substrate 210 thereby further exposing the underlying metal surface. In addition, hydrogen 224 is produced if the DC voltage applied is high enough, which can further promote a delamination process 226 (shown in FIG. 2) of the cathode by the mechanical action from evolved hydrogen burbles.

Figure 3:
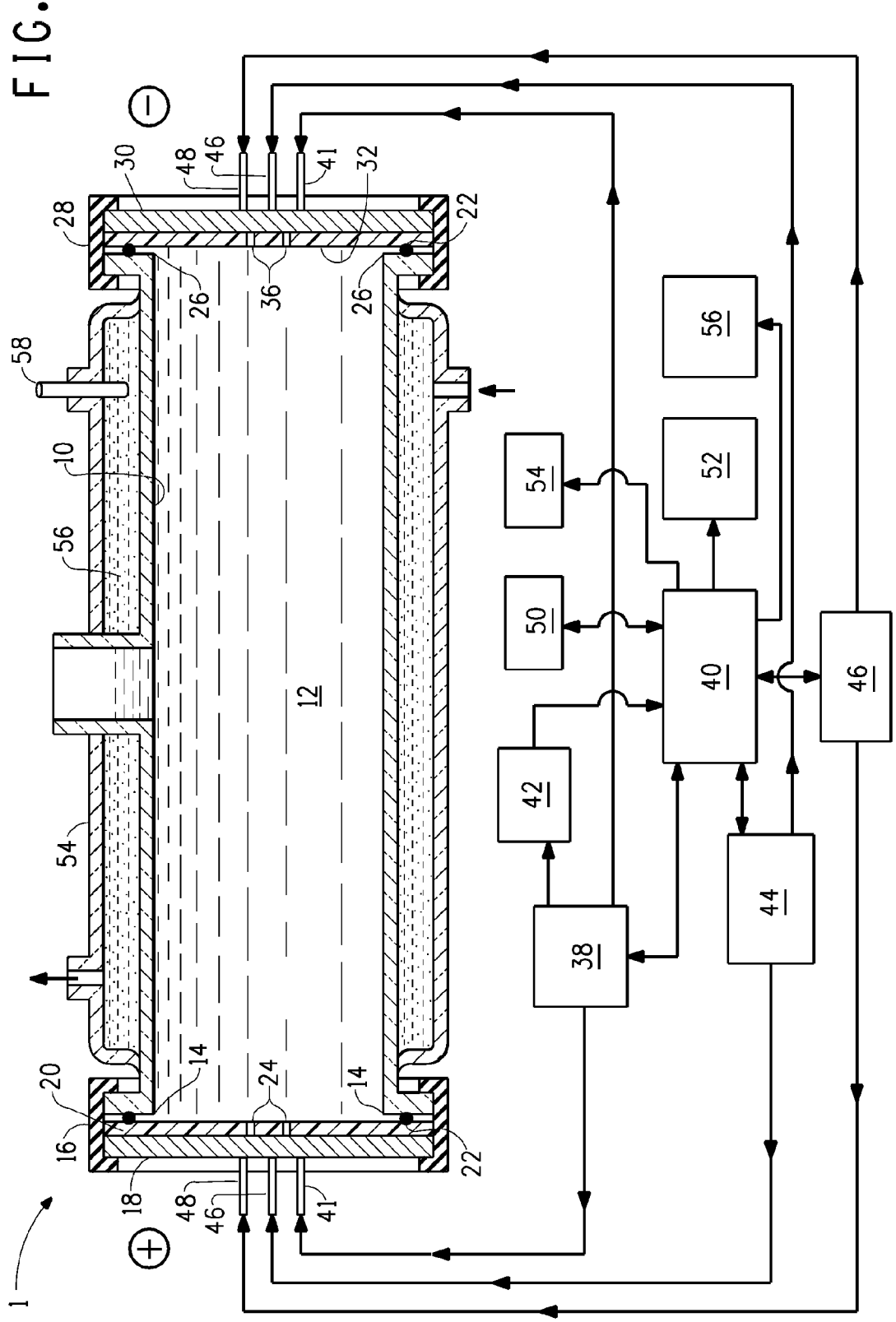
FIG. 3 illustrates a longitudinal cross-sectional view of one embodiment of the corrosion resistance evaluator of the present invention.

Therefore, it is necessary to develop a testing device and process therefor to expeditiously evaluate the corrosion resistance of protective coatings. One embodiment of a corrosion evaluator 1 for the present invention is shown in FIG. 3. Evaluator 1 includes a chamber 10, typically made of inert material, such as glass to retain an electrolyte 12 therein. Chamber 10 is preferably cylindrical in shape. Some of typical electrolytes can include an aqueous solution containing sodium chloride at a concentration of three parts by weight based on 100 parts by weight of the aqueous solution, or an aqueous solution that simulates acid rain or a corrosive chemical solution, such as those to which manufacturing equipment may be exposed to. Typically, the aqueous solution containing sodium chloride is preferably used.

One end of chamber 10 is provided with a flanged opening 14 over which an anode holder 16 can be mounted to retain an anode 18 made from various types of steel, aluminum, and copper. Anode 18 is coated with an anode coating 20 made of a single layer or a multilayer protective coatings resulting from an automotive OEM paint, automotive refinish paint, marine paint, aircraft paint, architectural paint, industrial paint, rubberized coating, polytetrafluoroethylene coating, or zinc-rich primer. One approach to prevent leaking of electrolyte 12 can be to provided an 'O' ring 22 retained in a circular groove on the flange of opening 14, whereby anode holder 16 retains anode 18 against 'O' ring 22. Anode holder 16 can be made of flexible material, such as rubber or it could be a clamp that grips anode 18. Anode coating 20 is provided with an anode defect 24 that exposes the surface of anode 18 to electrolyte 12.

A the other end of chamber 10 is provided with a flanged opening 26 over which a cathode holder 28 can be mounted to retain a cathode 30 made from various types of steel, aluminum, and copper. Cathode 30 is coated with a cathode coating 32 made of a single layer or a multilayer protective coatings resulting from an automotive OEM paint, automotive refinish paint, marine paint, aircraft paint, architectural paint, industrial paint, rubberized coating, polytetrafluoroethylene coating, or zinc-rich primer. One approach to prevent leaking of electrolyte 12 can be to provide an 'O' ring 22 retained in a circular groove on the flange of opening 26, whereby cathode holder 28 retains cathode 30 against 'O' ring 22. Cathode holder 28 can be made of flexible material, such as rubber or it could be a clamp that grips cathode 30. Cathode coating 32 is provided with a cathode defect 36 that exposes the surface of cathode 30 to electrolyte 12.

Evaluator 1 further includes a conventional direct current variable power generator 38 with DC output leads 41 that connect to anode 18 and cathode 30 such that desired DC voltages for desired durations can be applied across anode 18, cathode 30, and electrolyte 12. Direct current variable power generator 38 is also in communication with a conventional computer 40, such as the one supplied by Dell Computer Corporation of Round Rock, Tex. Evaluator 1 is provided with a conventional direct current measurement device 42 for measuring DC voltage applied across anode 18, cathode 30, and electrolyte 12. Direct current measurement device 42 is also in communication with computer 40.

Evaluator 1 further includes a conventional alternating current variable power generator 44 with AC output leads 46 that connect to anode 18 and cathode 30 for applying desired AC voltages at variable frequencies for desired durations across anode 18, cathode 30, and electrolyte 12. Alternating current variable power generator 44 is also in communication with computer 40. Generally, AC voltage applied is about 10 to 50 mV (milliVolt), 20 to 30 mV is preferred.

Evaluator 1 further includes a conventional impedance measurement device 46 with leads 48 that connect to anode 18 and cathode 30 for measuring impedance across anode 18, cathode 30, and electrolyte 12. Impedance measurement device 46 is also in communication with computer 40. The following explanation provides for the basic concept utilized in impedance measurements.

Impedance is a more general parameter that describes a circuit's ability to resist the flow of electrical current. An electrical current can be fully characterized by its amplitude and frequency characterized by a complex function. Similarly, the impedance is usually also described as a complex function. The impedance is more general, since it also covers the case of DC current by simply assuming the frequency (f) is zero.

The impedance (Z) of a circuit can be described by the combination of three ideal electrical elements, namely inductor (L), capacitor (C), and resistor (R) by the following equations:

$$Z(L)=j2\pi fL \qquad (3)$$

$$Z(C)=-j1/(2\pi fC) \qquad (4)$$

$$Z(R)=R \qquad (5).$$

Where: f is the frequency in Hz
L is the quantity of the inductance
C is the quantity of the capacitance
J is a symbol of complex function; $\sqrt{-1}$ It can be shown that the impedance of a resistor is independent of frequency, while the impedance of an inductor is increased as a function of frequency and the impedance of a capacitor is inversely proportional to the frequency. As mentioned above, in most cases, the impedance (Z) of a circuit is usually the combination of three ideal electrical elements and the actual impedance can be described by the following complex function:

$$Z \cdot (L,C,R)=Z(L)+Z(C)+Z(R)=R+j(2\pi fL-1/(2\pi fC))=\text{real part}+j \text{ imaginary part} \qquad (6)$$

Figure 4A:
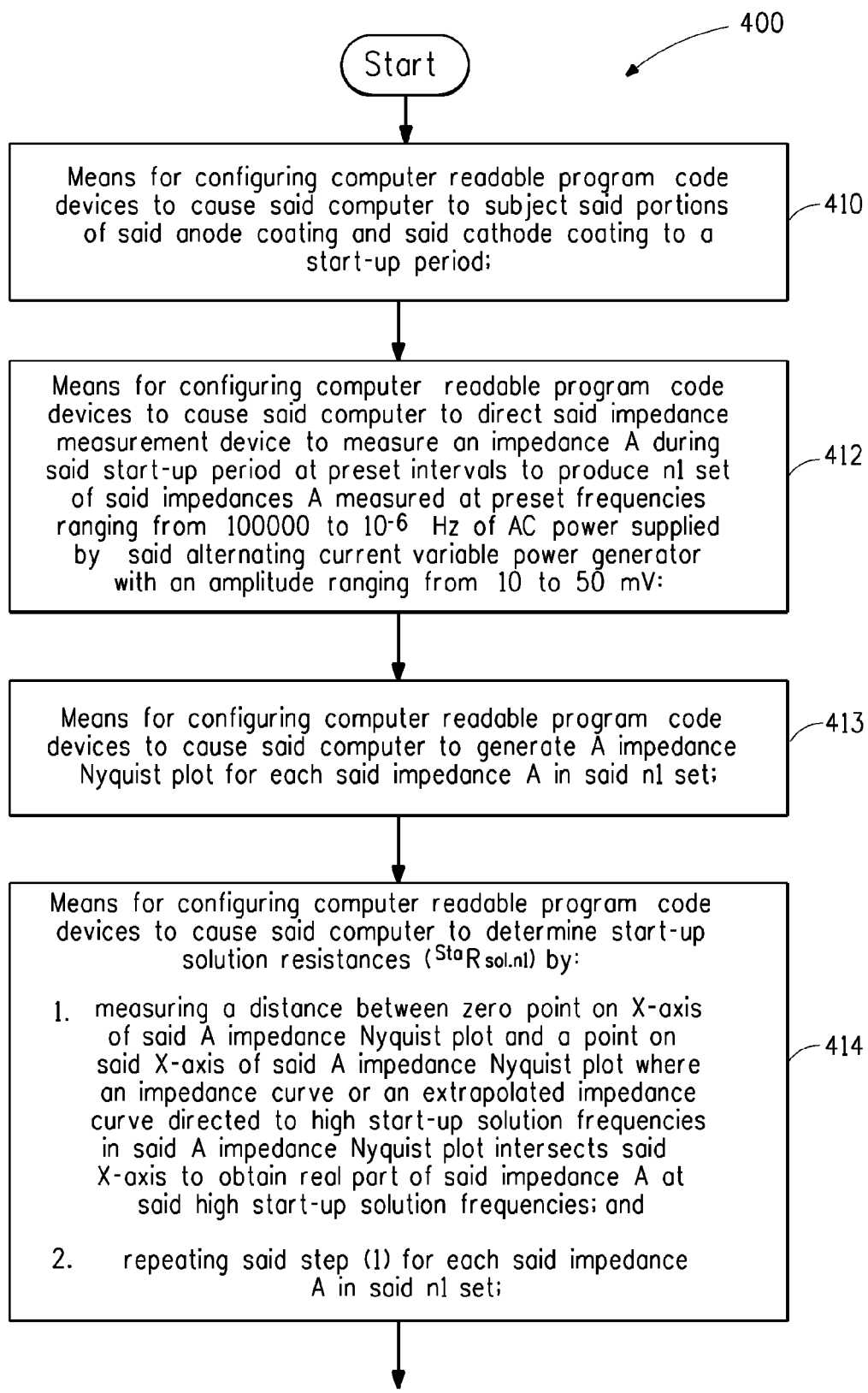
Figure 4C:
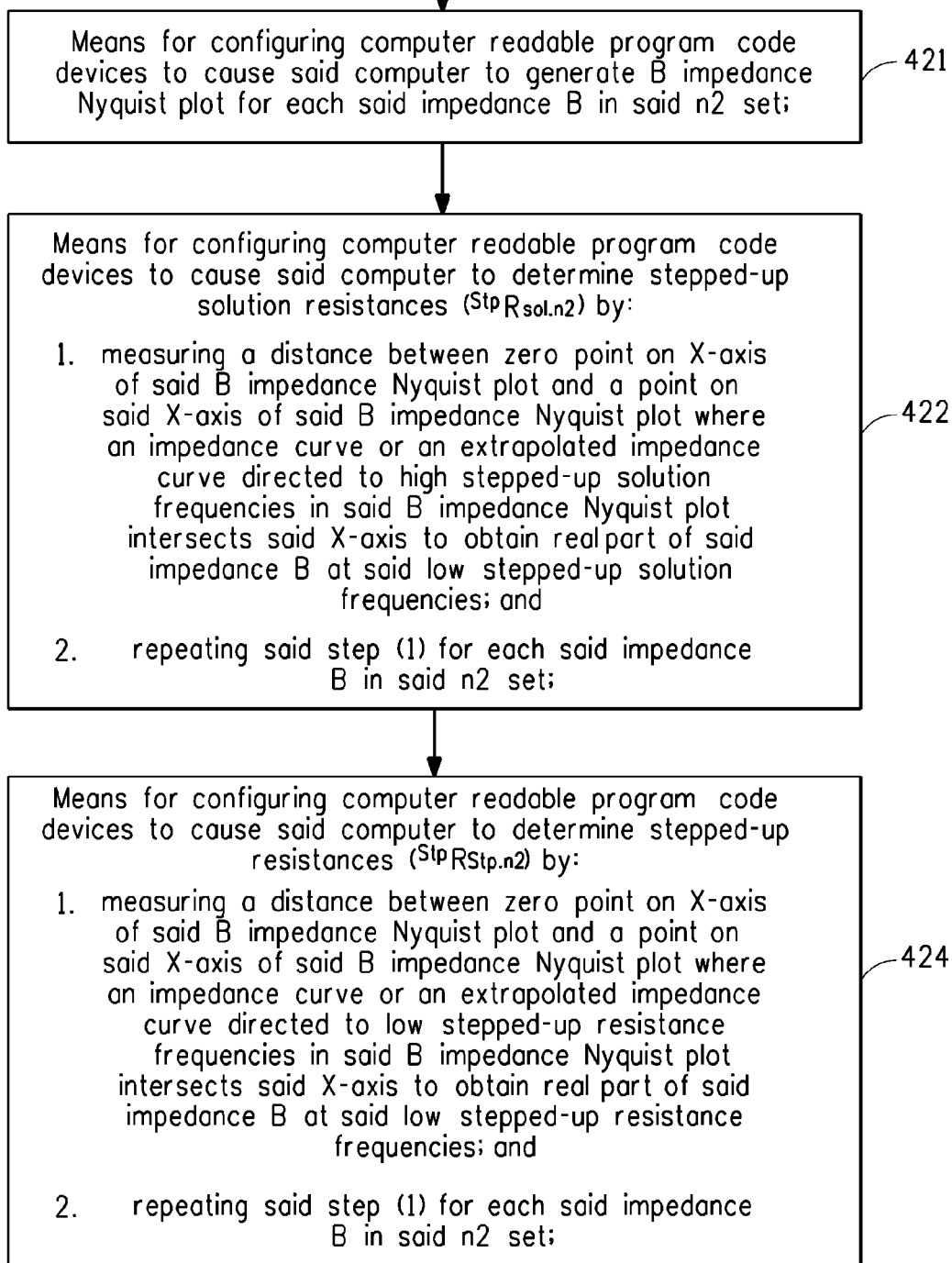
Figure 4D:
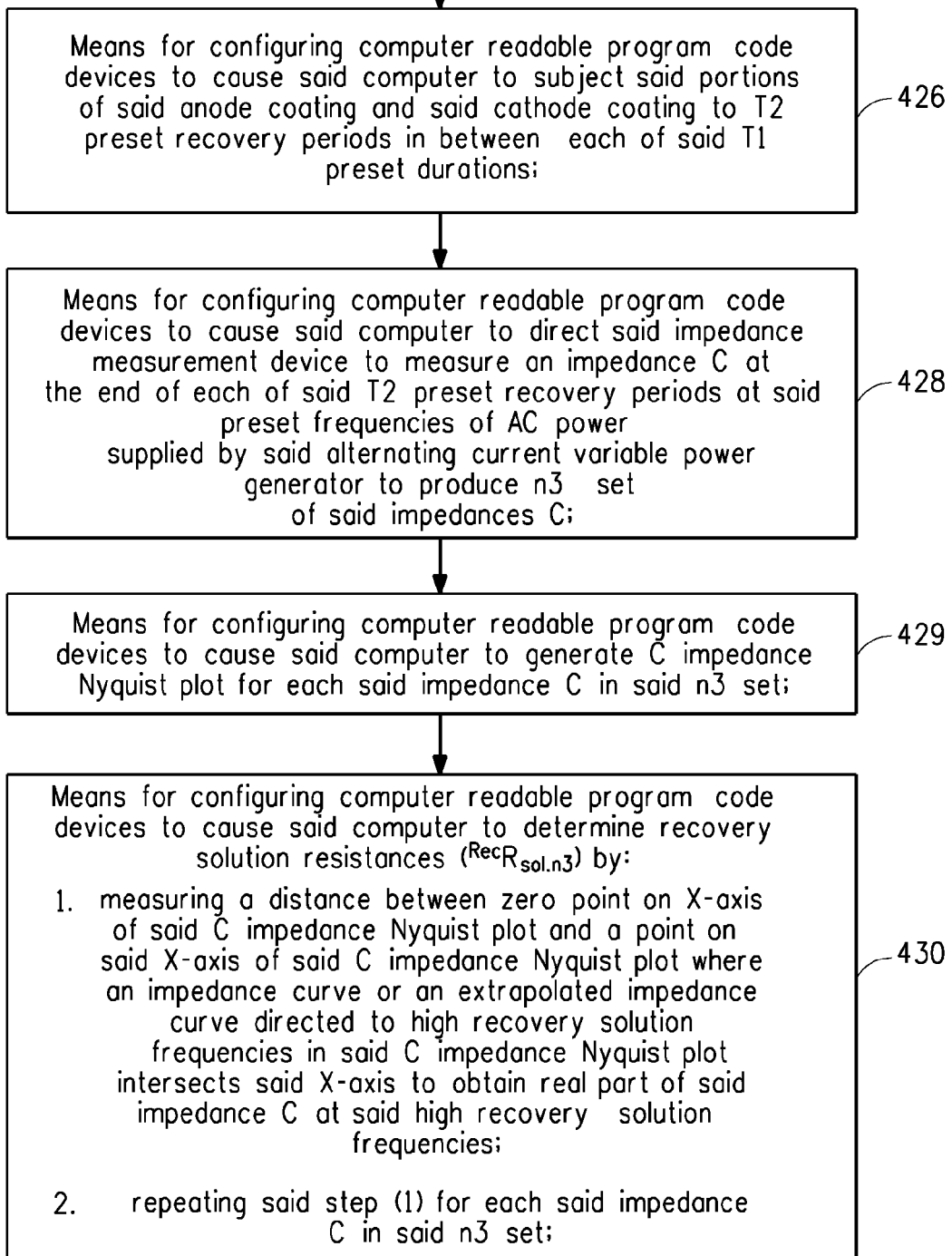

Evaluator 1 further includes a computer usable storage medium 50 located in computer 40, which is in communication with direct current variable power generator 38, direct current measurement device 42, alternating current variable power generator 44 and impedance measurement device 46, wherein computer readable program code means 400 (described in FIGS. 4A, 4B. 4C, 4D, 4E and 4F) reside in said computer usable storage medium 50.

Figure 10:
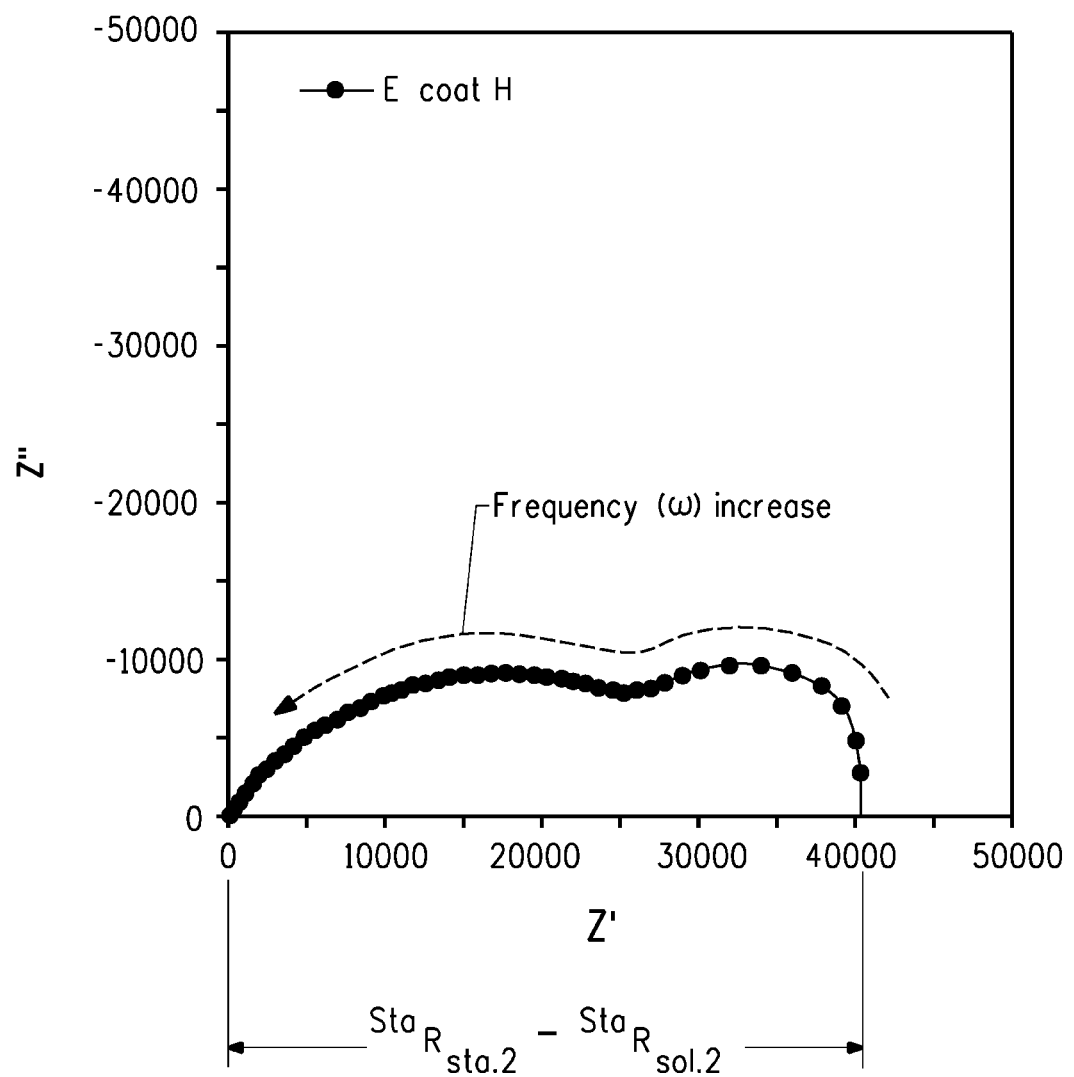
FIG. 10 illustrates A impedance Nyquist plot for impedance A obtained on E-coat H during start up period.
Figure 11:
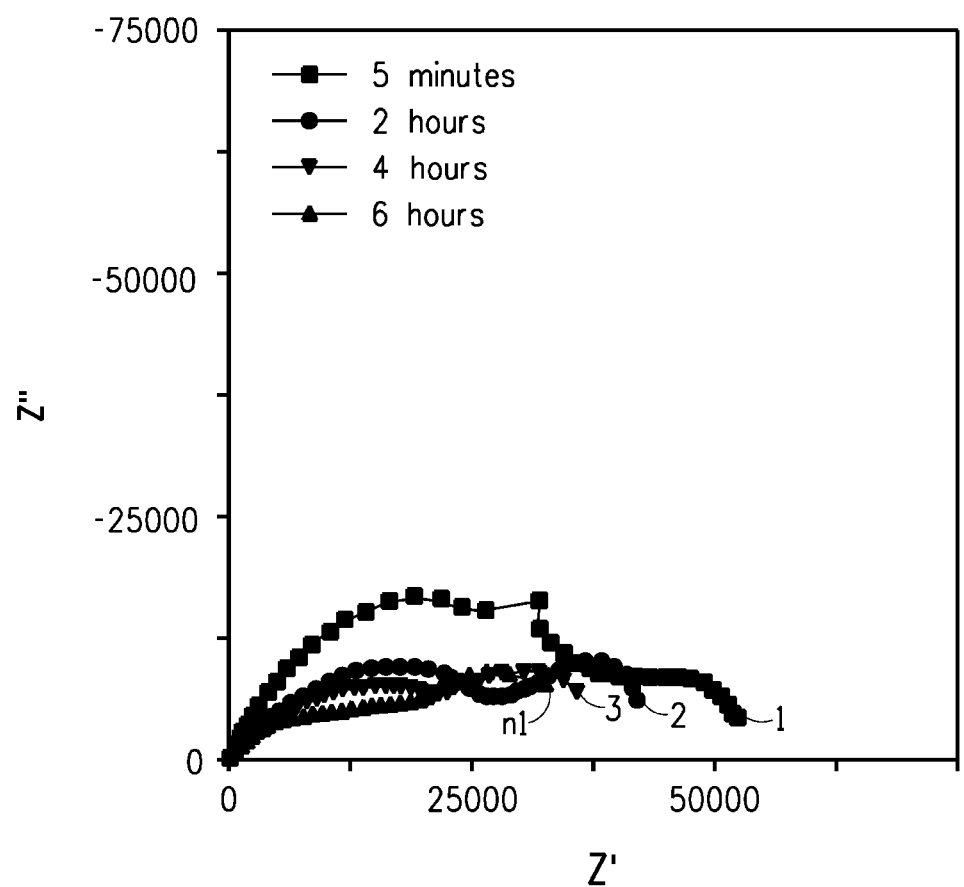
FIG. 11 illustrates the n1 set of the A impedance Nyquist plots of A impedances obtained.
Figure 12:
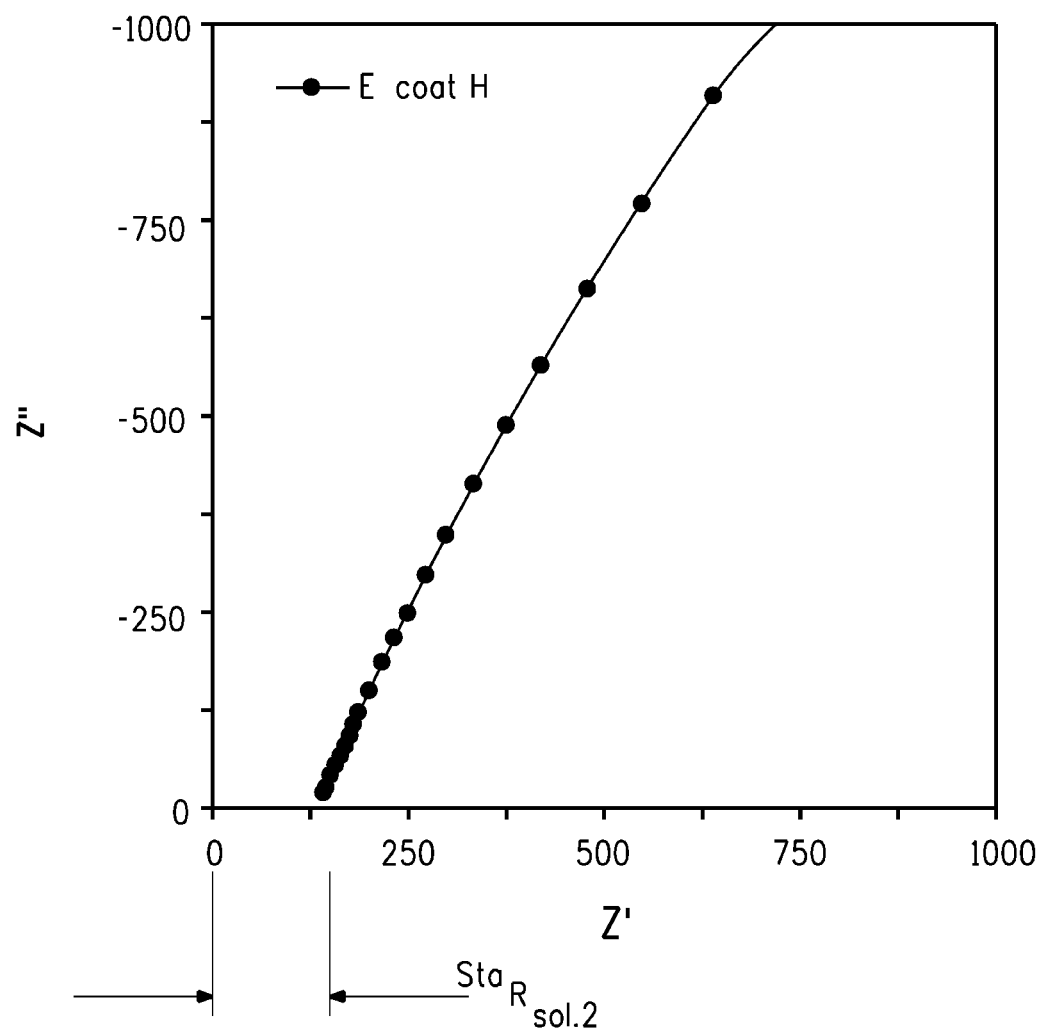
FIG. 12 illustrates the expanded left part of the A impedance Nyquist plot of impedance A of FIG. 10 at high start-up solution frequencies.

Computer Readable Program Code Means 400 Include:

means 410 for configuring computer readable program code devices to cause computer 40 to subject said portions of anode coating 20 and cathode coating 32 to a start-up period, which can range from half an hour to one thousand hours, preferably from 3 to 15 hours.

means 412 for configuring computer readable program code devices to cause computer 40 to direct impedance measurement device 46 to measure an impedance A during said start-up period at preset intervals to produce n1 set of said impedances A measured at preset frequencies ranging from 100000 to $10^{-6}$ Hz of AC power supplied by alternating current variable power generator 44 with an amplitude ranging from 10 to 50 mV. The preset interval ranges from half an hour to ten hours.

means 413 for configuring computer readable program code devices to cause computer 40 to generate A impedance Nyquist plot for each said impedance A in said n1 set as seen in FIGS. 10 and 11.

means 414 for configuring computer readable program code devices to cause computer 40 to determine start-up solution resistances ($^{Sta}R_{sol.n1}$) by:
1. measuring, as seen in FIG. 12, a distance between zero point on X-axis of said A impedance Nyquist plot and a point on said X-axis of said A impedance Nyquist plot where an impedance curve or an extrapolated impedance curve directed to high start-up solution frequencies in said A impedance Nyquist plot intersects said X-axis to obtain real part of said impedance A at said high start-up solution frequencies; and
2. repeating said step (1) for each said impedance A in said n1 set.

Figure 13:
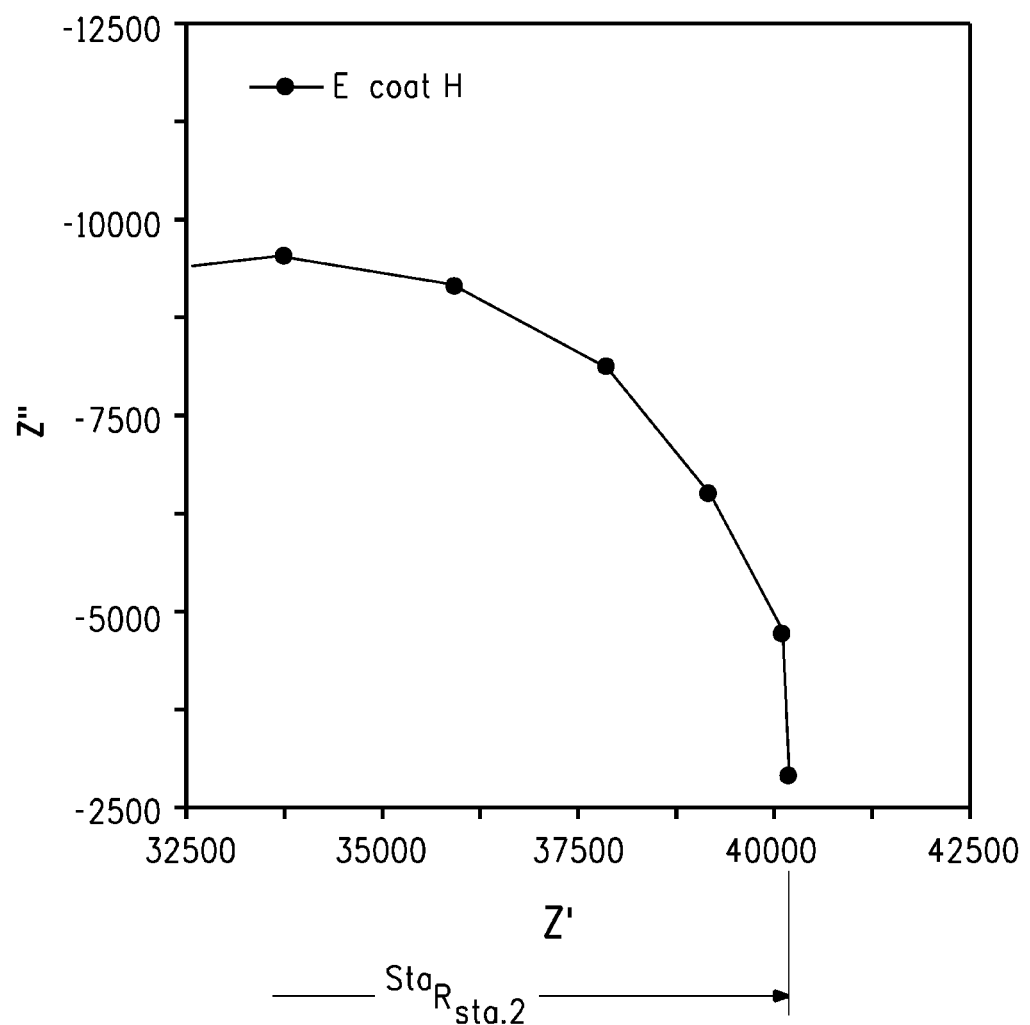
FIG. 13 illustrates the expanded right part of the A impedance Nyquist plot of impedance A of FIG. 10 at low start-up resistance frequencies.

The high start-up solution frequencies can range from about 500 to about 100000 Hz, preferably from about 5000 to about 10000 Hz.

means 416 for configuring computer readable program code devices to cause computer 40 to determine start-up resistances ($^{Sta}R_{Sta.n1}$) by:
1. measuring, as seen in FIG. 13, a distance between zero point on X-axis of said A impedance Nyquist plot and a point on said X-axis of said A impedance Nyquist plot where an impedance curve or an extrapolated impedance curve directed to low start-up resistance frequencies in said A impedance Nyquist plot intersects said X-axis to obtain real part of said impedance A at said low start-up resistance frequencies; and
2. repeating said step (1) for each said impedance A in said n1 set.

Figure 5:
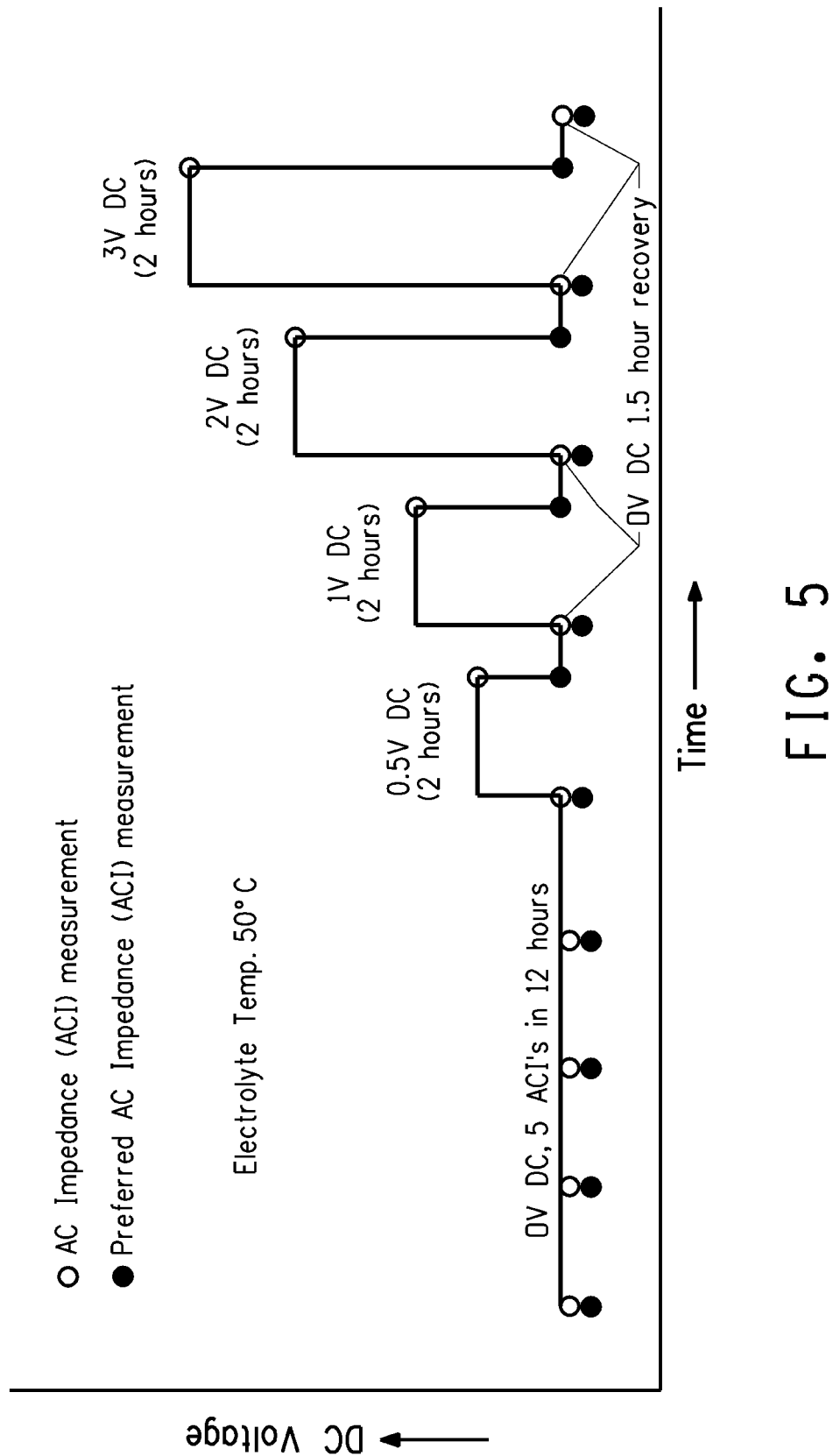
FIG. 5 illustrates one of the typical protocols used in the process of the present invention.

The low start-up resistance frequencies can range from about $10^{-1}$ to about $10^{-6}$ Hz, preferably from about $10^{-2}$ to about $10^{-3}$ Hz.

means 418 for configuring computer readable program code devices to cause computer 40 to direct current variable power generator 38 to apply V1 preset DC voltages in a stepwise manner for T1 preset durations, wherein direct current measurement device 42 in communication with computer 40 and connected to cathode 30 and anode 18 is used to measure said preset DC voltages and wherein the V1 preset DC voltage ranges from 0.1 millivolts to 10 volts, preferably from 0.5 volts to four volts, typically with half a volt increments. The T1 preset duration ranges from half an hour to 100 hours. The higher the DC voltage lower should be the preset duration and the lower DC voltage higher should be the preset duration. It should be understood that T1 preset duration can be same for all steps or it may be increased or decreased from step to step, if so desired. FIG. 5 illustrates the typical protocols used in the process of the present invention, which is directed to a stepwise form.

means 420 for configuring computer readable program code devices to cause computer 40 to direct impedance measurement device 46 to measure an impedance B at the end of each of said preset duration at said preset frequencies of AC power supplied by alternating current variable power generator 44 to produce n2 set of said impedances B.

means 421 for configuring computer readable program code devices to cause computer 40 to generate B impedance Nyquist plot for each said impedance B in said n2 set. These Nyquist plots would be similar to those described earlier in FIGS. 10 through 13.

means 422 for configuring computer readable program code devices to cause computer 40 to determine stepped-up solution resistances ($^{Stp}R_{sol.n2}$) by:
1. measuring a distance between zero point on X-axis of said B impedance Nyquist plot and a point on said X-axis of said B impedance Nyquist plot where an impedance curve or an extrapolated impedance curve directed to high stepped-up solution frequencies in said B impedance Nyquist plot intersects said X-axis to obtain real part of said impedance B at said high stepped-up solution frequencies; and
2. repeating said step (1) for each said impedance B in said n2 set.

The high stepped-up solution frequencies can range from about 500 to about 100000 Hz, preferably from about 5000 to about 10000 Hz.

means 424 for configuring computer readable program code devices to cause computer 40 to determine stepped-up resistances ($^{Sta}R_{Stp.n2}$) by:
1. measuring a distance between zero point on X-axis of said B impedance Nyquist plot and a point on said X-axis of said B impedance Nyquist plot where an impedance curve or an extrapolated impedance curve directed to low stepped-up resistance frequencies in said B impedance Nyquist plot intersects said X-axis to obtain real part of said impedance B at said low stepped-up resistance frequencies; and
2. repeating said step (j) (1) for each said impedance B in said n2 set;

The low stepped-up resistance frequencies can range from about $10^{-1}$ to about $10^{-6}$ Hz, preferably from about $10^{-2}$ to about $10^{-3}$ Hz.

means 426 for configuring computer readable program code devices to cause computer 40 to subject the portions of anode coating 20 and cathode coating 32 to T2 preset recovery periods in between each of said T1 preset durations. Typically, T2 preset recovery periods range from half an hour to ten hours, preferably ranging from 30 minutes to 3 hours. It should be understood that T2 preset recovery period can be same for all the steps or it may be increased or decreased from step to step, if so desired.

means 428 for configuring computer readable program code devices to cause computer 40 to direct impedance measurement device 46 to measure an impedance C at the end of each of the T2 preset recovery periods at the preset frequencies of AC power supplied by alternating current variable power generator 44 to produce n3 set of the impedances C.

means 429 for configuring computer readable program code devices to cause computer 40 to generate C impedance Nyquist plot for the said impedance C in the n3 set. These Nyquist plots would be similar to those described earlier in FIGS. 10 through 13.

means 430 for configuring computer readable program code devices to cause computer 40 to determine recovery solution resistances ($^{Rec}R_{sol.n3}$) by:
1. measuring a distance between zero point on X-axis of said C impedance Nyquist plot and a point on X-axis of said C impedance Nyquist plot where an impedance curve or an extrapolated impedance curve directed to high recovery solution frequencies in said C impedance Nyquist plot intersects said X-axis to obtain real part of said impedance C at said high recovery solution frequencies;

2. repeating said step (1) for each said impedance C in said n3 set;

The high recovery solution frequencies can range from about 500 to about 100000 Hz, preferably from about 5000 to about 10000 Hz.

means 432 for configuring computer readable program code devices to cause computer 40 to determine recovery resistances ($^{Rec}R_{Rec.n3}$) by:

1. measuring a distance between zero point on X-axis of said C impedance Nyquist plot and a point on said X-axis of said C impedance Nyquist plot where an impedance curve or an extrapolated impedance curve directed to low recovery resistance frequencies in said C impedance Nyquist plot intersects said X-axis to obtain real part of said impedance C at said low recovery resistance frequencies; and 2. repeating said step (1) for each said impedance C in said n3 set;

The low recovery resistance frequencies can range from about $10^{-1}$ to about $10^{-6}$ Hz, preferably from about $10^{-2}$ to about $10^{-3}$ Hz.

means 434 for configuring computer readable program code devices to cause computer 40 to calculate corrosion performance resistance ($R_{perf}$) of anode 18 and cathode 30 pair by using the following equation:

$$R_{perf} = [\Sigma f_{n1}(^{Sta}R_{Sta.n1} - ^{Sta}R_{Sol.n1})]/n1 + [\Sigma^{Stp} f_{n2} (^{Stp}R_{Stp.n2} - ^{Stp}R_{Sol.n2})]/n2 + [\Sigma^{Rec} f_{n3}(^{Rec}R_{Rec.n3} - ^{Rec}R_{Sol.n3})]/n3,$$

wherein n1, n2, n3 and n3 range from 1 to 100, preferably n1 ranges from 5 to 15, n2 and n3 range from 3 to 10; and $^{Sta}f_{n1}$, $^{Stp}f_{n2}$, and $^{Rec}f_{n3}$ range from 0.0000001 to 1, preferably range from 0.1 to 1. Generally, n2 is equal to n3. By way of clarification, if n1 is 5, then inside sigma ($\Sigma$), n1 in the numerator would be 1, 2, 3, 4, and 5 and n1 in the denominator would be 5.

means 436 for configuring computer readable program code devices to cause computer 40 to:

(q1) direct a computer monitor to display said corrosion performance resistance ($R_{perf}$);

(q2) direct a printer to print said corrosion performance resistance ($R_{perf}$);

(q3) transfer said corrosion performance resistance ($R_{perf}$) to a remote computer or a remote database; or (q4) a combination thereof.

FIG. 5 illustrates one of the typical protocols used in the process of the present invention. Total time for performing the test can range from 2 hours to 350 hours, preferably 20 hours to 40 hours.

Preferably, direct current variable power generator 38, direct current measurement device 42, alternating current variable power generator 44 and impedance measurement device 46 can all be positioned in a single stand-alone unit for convenience and ease of operation. Such a unit was obtained from Solartron Analytical located at Farnborough, Hampshire, United Kingdom. The following website can be accessed to get further information on these devices (http://www.solartronanalytical.com/index.htm).

Figure 6:
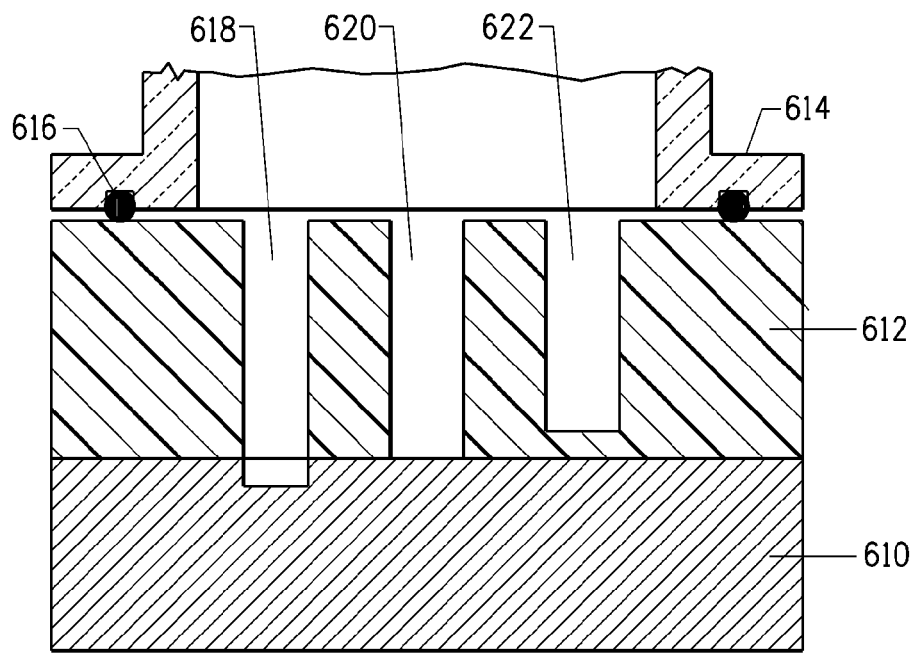
FIGS. 6 and 7 illustrate the deliberately created artificial defects on anode and cathode coatings for exposing the underlying surface of metal anodes and cathodes.

In order to eliminate the effect of random intrinsic defects of coatings, applicants made a surprising discovery that by deliberately creating the standardized defects of known sizes and shapes on cathode and anode coatings and exposing the underlying anode/cathode surface to an electrolyte, the anodic dissolution of the underlying anodes and the delamination process of the underlying cathodes can be substantially accelerated in a predictable and reproducible manner when DC voltage are applied across the cathode and anode. FIG. 6 illustrates such deliberately created defects 618, 620, and 622 on anode or cathode coating 612 applied over a cathode or anode 610 that is positioned against chamber 614 having an 'O' ring 616. The most desirable defect is defect 620, although Defect 618 is acceptable since it does expose the underlying surface of cathode or anode 610 to the electrolyte, whereas defect 622 is unacceptable as it does not expose the underlying surface of cathode or anode 610 to the electrolyte.

Figure 7:
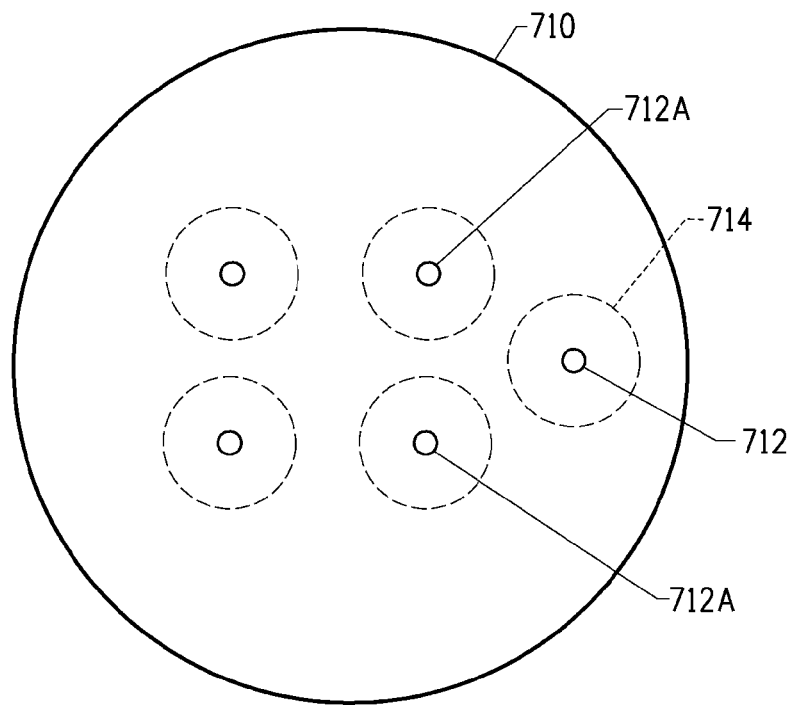

Preferably, anode or cathode defect, as illustrated in FIG. 7 include a plurality of circular openings 712 disposed on coating 710 that expose the underlying surface of the anode or cathode to the electrolyte. Circular openings 712 have a diameter in the range of from 5 micrometers to 5 millimeters, 5 micrometers to 1 millimeter being preferred, each circular opening 712 being uniformly separated from one another by 10 to 2000 times the diameter of circular openings 712. As a result, corrosion effect illustrated by a zone 714 on one opening 712 does not spill over and affect the corrosion process on an adjacent opening 712A. Alternatively, anode or cathode coating 710 can be provided with 1 to 100 of circular openings 712 per square centimeter of said cathode or anode.

Preferably, anode 18 and cathode 30 have identical shape (preferably circular) and thickness. Preferably, anode coating 20 is identical to cathode coating 32 and preferably, anode defect 24 is identical to cathode defect 36. As a result, any deviations between the set of cathode and anode can be eliminated.

Evaluator 1 can be provided with a thermal jacket 54 to maintain the temperature of electrolyte 12 at a desired temperature. Typically, a heat transfer fluid 56, such as water can be used to maintain the temperature of electrolyte 12 in the range of 0.5° C. to 99.5° C. A conventional temperature probe 58 in communication with computer 40 can be used to maintain the temperature of electrolyte 12 at a desired temperature.

Figure 8:
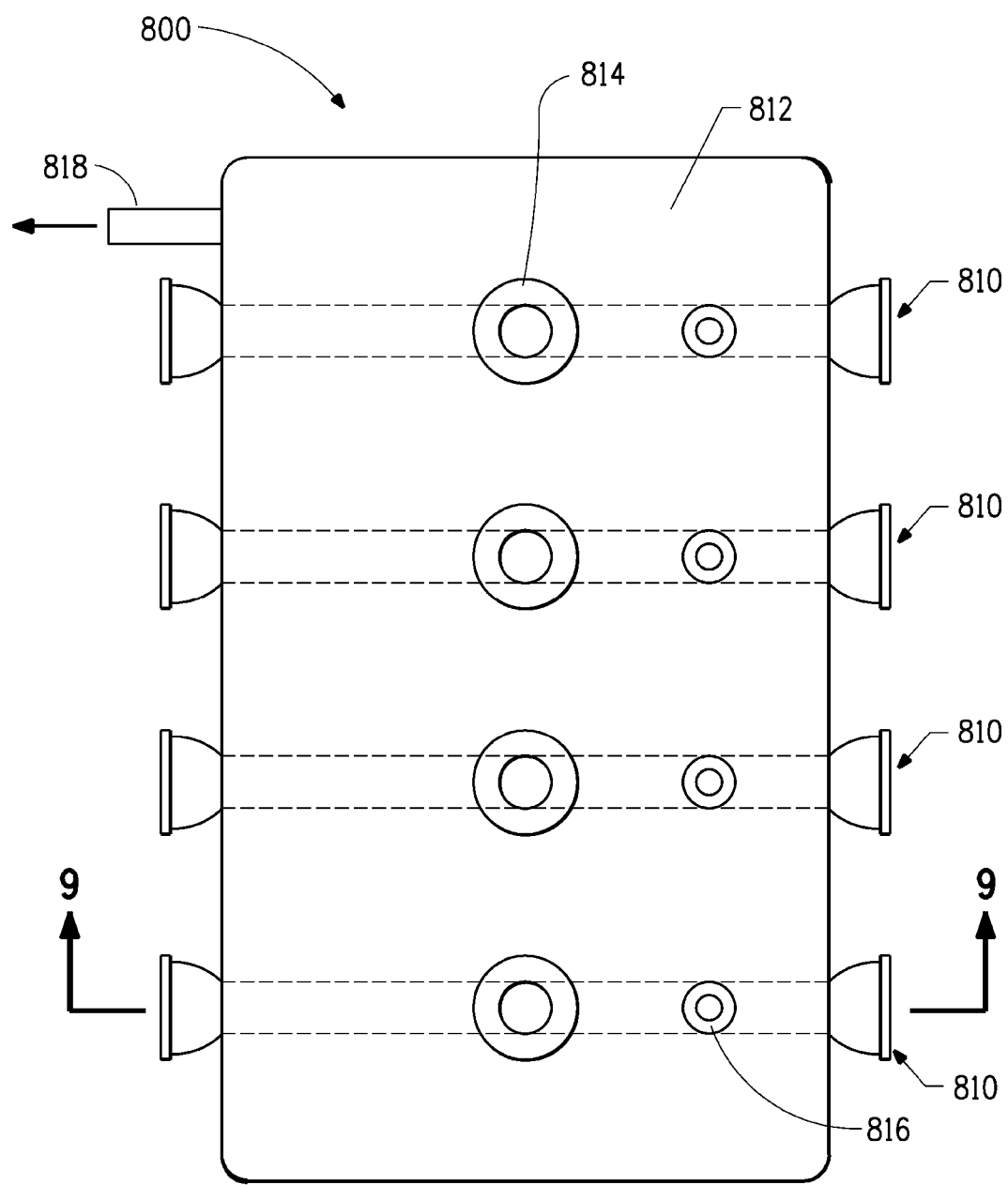
FIG. 8 illustrates a plan view of yet another embodiment of the present invention that provides for multiple chambers.

Evaluator 1 can be configured to provide two or more chambers whereby all such chambers can be maintained under similar conditions for comparing the corrosion resistance of one set of protective coatings against other, i.e., cathodes having different types of cathode coatings applied thereon can be compared for coating delamination performance (the lesser the delamination the better will be coating corrosion resistance properties). Similarly, anodes paired with corresponding cathodes having identical anode coatings applied thereon can be compared for corrosion resistance of one type of said anode coating to the other type of said anode coating. Preferably, each paired cathode and anode will have identical coating applied thereon. FIG. 8 illustrates multi-chamber 800 construct whereby chambers 810 are enclosed within a thermal jacket 812.

Figure 9:
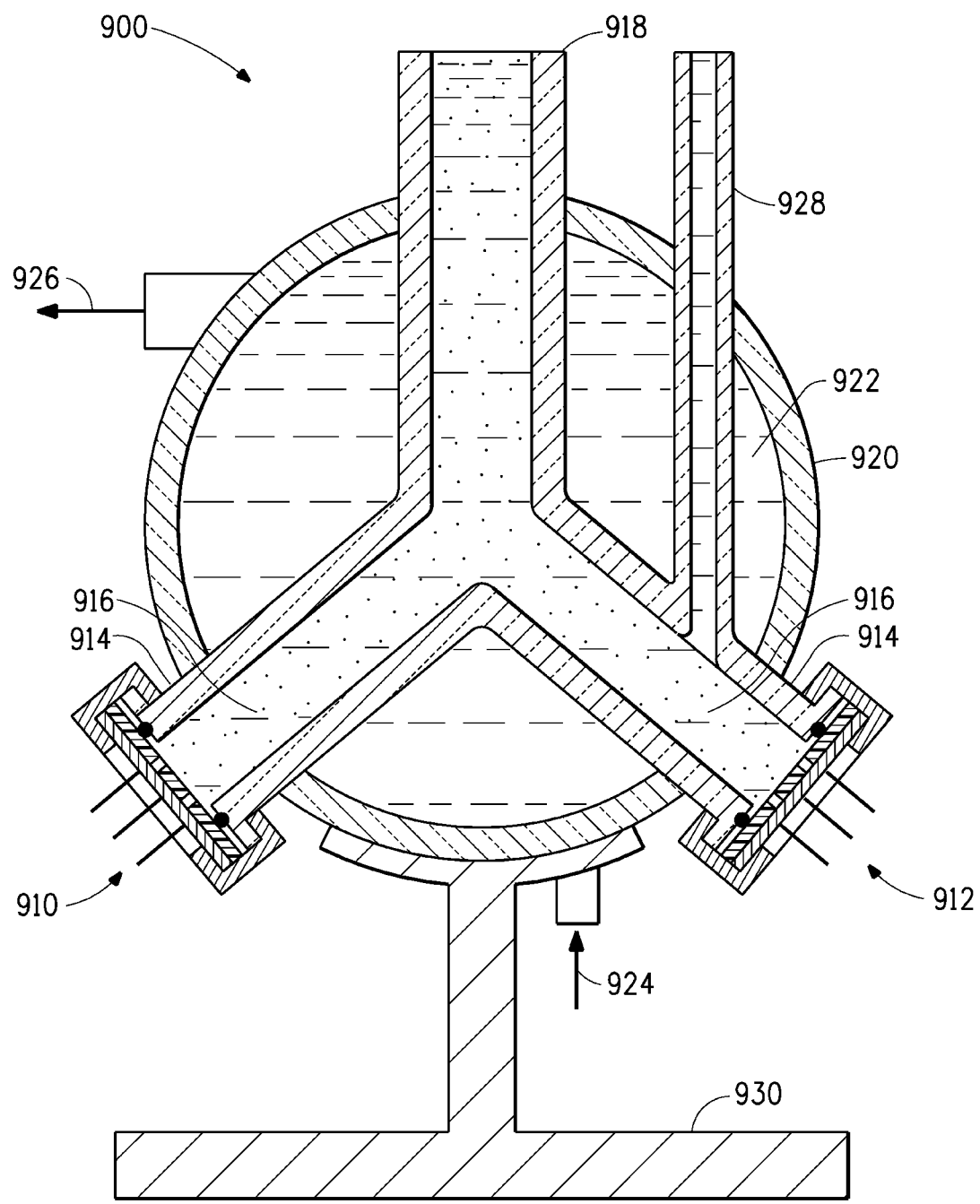
FIG. 9 illustrates a plan view of yet another embodiment of the present invention that provides for expeditious escape of gases generated during the corrosion testing process.

Another embodiment of the present invention 900, shown in FIG. 9, includes anode assembly 910 and cathode assembly 912 forming a leg 914 of an inverted 'Y' ($\lambda$) to permit any gas generated in electrolyte 916 during use or gas bubbles adhered on the surface of coated coupons during installation to escape readily from a cylindrical chamber 918, which can be provided with a thermal jacket 920 containing heat transfer fluid 922 having an inlet 924 and an outlet 926. Chamber 918 can be further provided with a thermometer well 928 and a support 930.

In the alternative, applicants also contemplate another embodiment of the present invention wherein a chamber in the form of inverted 'U' (∩) with the anode and cathode positioned at the bottom of each leg of the inverted 'U' shaped chamber having an opening at the apex of the inverted 'U' shaped chamber to permit any gas generated in the electrolyte during use to escape readily from the chamber.

The present invention is also directed to a process that utilizes the evaluator 1 descried in FIG. 3. The process evaluates the corrosion resistance anode coating 20 applied over a surface of anode 18 and corrosion resistance of cathode coating 32 applied over a surface of cathode 30 by utilizing the following steps:

(i) sealably positioning anode 18 in anode holder 16 located on chamber 10 of corrosion resistance evaluator 1, chamber 10 containing electrolyte 12 therein such that a portion of anode coating 20 is exposed to electrolyte 12, the portion of anode coating 20 having anode defect 24 thereon;

(ii) sealably positioning cathode 30 in cathode holder 28 located on chamber 10 such that a portion of cathode coating 32 is exposed to electrolyte 12, the portion of cathode coating 32 having cathode defect 36 thereon;

(iii) directing computer 40 of evaluator 1 through computer readable program code means 400 (shown in FIGS. 4A, 4B, 4C, 4D, 4E and 4F) residing on usable storage medium 50 located in computer 40 and configured to cause computer 40 to perform following steps comprising:

a. subjecting the portions of anode coating 20 and cathode coating 30 to a start-up period;

b. directing impedance measurement device 46 in communication with computer 40 and is connected to cathode 30 and anode 18 to measure an impedance A during said start-up period at preset intervals to produce n1 set of said impedances A measured at preset frequencies ranging from 100000 to $10^{-6}$ Hz of AC power with an amplitude ranging from 10 to 50 mV supplied by alternating current variable power generator 44 in communication with computer 40, alternating current variable power generator 44 having AC output leads 46 that connect to cathode 30 and anode 18;

c. generating A impedance Nyquist plot for each said impedance A in said n1 set;

d. determining start-up solution resistances ($^{Sta}R_{sol.n1}$) by:
  1. measuring a distance between zero point on X-axis of said A impedance Nyquist plot and a point on said X-axis of said A impedance Nyquist plot where an impedance curve or an extrapolated impedance curve directed to high start-up solution frequencies in said A impedance Nyquist plot intersects said X-axis to obtain real part of said impedance A at said high start-up solution frequencies; and
  2. repeating said step (d) (1) for each said impedance A in said n1 set;

e. determining start-up resistances ($^{Sta}R_{Sta.n1}$) by:
  1. measuring a distance between zero point on X-axis of said A impedance Nyquist plot and a point on said X-axis of said A impedance Nyquist plot where an impedance curve or an extrapolated impedance curve directed to low start-up resistance frequencies in said A impedance Nyquist plot intersects said X-axis to obtain real part of said impedance A at said low start-up resistance frequencies; and
  2. repeating said step (e) (1) for each said impedance A in said n1 set;

f. directing direct current variable power generator 38 to apply V1 preset DC voltages in a stepwise manner for T1 preset durations, wherein direct current measurement device 42 in communication with computer 40 and connected to cathode 30 and anode 18 is used to measure said preset DC voltages and wherein said V1 preset DC voltage ranges from 0.1 millivolts to 10 volts and said T1 preset duration ranges from half an hour to 100 hours;

g. directing impedance measurement device 46 to measure a set of impedances B at the end of each of said preset duration at said preset frequencies of AC power supplied by alternating current variable power generator 44 to produce n2 said sets of said impedances B;

h. generating B impedance Nyquist plot for each said impedance B in said n2 set;

i. determining stepped-up solution resistances ($^{Stp}R_{sol.n2}$) by:
  1. measuring a distance between zero point on X-axis of said B impedance Nyquist plot and a point on said X-axis of said B impedance Nyquist plot where an impedance curve or an extrapolated impedance curve directed to high stepped-up solution frequencies in said B impedance Nyquist plot intersects said X-axis to obtain real part of said impedance B at said high stepped-up solution frequencies;
  2. repeating said step (i) (1) for each said impedance B in said n2 set;

j. determining stepped-up resistances ($^{Stp}R_{Stp.n2}$) by:
  1. measuring a distance between zero point on X-axis of said B impedance Nyquist plot and a point on said X-axis of said B impedance Nyquist plot where an impedance curve or an extrapolated impedance curve directed to low stepped-up resistance frequencies in said B impedance Nyquist plot intersects said X-axis to obtain real part of said impedance B at said low stepped-up resistance frequencies; and
  2. repeating said step (j) (1) for each said impedance B in said n2 set;

k. subjecting said portions of anode coating 20 and cathode coating 32 to T2 preset recovery periods in between each of said T1 preset durations;

l. directing impedance measurement device 46 to measure an impedance C at the end of each of said T2 preset recovery periods at said preset frequencies of AC power supplied said alternating current variable power generator 44 to produce n3 set of said impedances C;

m. generating C impedance Nyquist plot for each said impedance C in said n3 set;

n. determining recovery solution resistances ($^{Rec}R_{sol.n3}$) by:
  1. measuring a distance between zero point on X-axis of said C impedance Nyquist plot and a point on said X-axis of said C impedance Nyquist plot where an impedance curve or an extrapolated impedance curve directed to high recovery solution frequencies in said C impedance Nyquist plot intersects said X-axis to obtain real part of said impedance C at said high recovery solution frequencies;
  2. repeating said step (n) (1) for each said impedance C in said n3 set;

o. determining recovery resistances ($^{Rec}R_{Rec.n3}$) by:
  1. measuring a distance between zero point on X-axis of said C impedance Nyquist plot and a point on said X-axis of said C impedance Nyquist plot where an impedance curve or an extrapolated impedance curve directed to low recovery resistance frequencies in said C impedance Nyquist plot intersects said X-axis to obtain real part of said impedance C at said low recovery resistance frequencies; and 2. repeating said step (o) (1) for each said impedance C in said n3 set;

p. calculating corrosion performance resistance ($R_{perf}$) of said anode and said cathode pair by using the following equation:

$$R_{perf}=[\Sigma^{Sta}f_{n1}(^{Sta}R_{Sta.n1}-^{Sta}R_{Sol.n1})]/n1+[\Sigma^{Stp}f_{n2}(^{Stp}R_{Sol.n2}-^{Stp}R_{Sol.n2})]/n2+[\Sigma^{Rec}f_{n3}(^{Rec}R_{Rec.n3}-^{Rec}R_{Sol.n3})]/n3,$$

wherein n1, n2, n3 and n3 range from 1 to 100; and $^{Sta}f_{n1}$, $^{Stp}f_{n2}$, and $^{Rec}f_{n2}$ range from 0.0000001 to 1; and q. causing computer 40 to direct a computer monitor 52 to:
  (q1) display the corrosion performance resistance ($R_{perf}$),
  (q2) direct a printer 54 to print the corrosion performance resistance ($R_{perf}$),
  (q3) transfer the corrosion performance resistance ($R_{perf}$) to a remote computer 56 or a remote database, or
  (q4) a combination thereof.

The process of the present invention can be used comparing the corrosion resistance of one type of coating against another type of coating by testing them under similar conditions and protocol by utilizing multiple chambers such as those shown in FIG. 8. Cathodes having different types of cathode coatings applied thereon and said anodes having different types of anode coatings applied thereon can be compared to evaluate delamination resistance of one type of cathode coating to the other type of cathode coating. It should be understood that each set of paired cathode and anode would have identical coating applied thereon. Simultaneously, anodes having different types of anode coatings applied thereon can be compared to evaluate corrosion resistance of one type of anode coating to the other type of anode coating.

EXAMPLES

Comparative Corrosion Data from Conventional Corrosion Test Method

The correlation between a conventional 40-day cyclic corrosion test and the corrosion test of the present invention was performed by using eight conventional E-coat systems. To vary the corrosion performance, eight E-coating systems designated as coating A, B, C, D, F, G, H and I comprising different phosphate pretreatments, different formulations, different baking temperatures and baking times were applied on test panels made of cold rolled steel. All the test panels were identical in size, shape and thickness. A coated test panel was defined as a coupon. After coating was applied and cured, each coupon was scribed with grid pattern. The conventional 40-day cyclic corrosion test used in the correlation verification utilized 40 cycles of the corrosion test. Each cycle lasting 24 hours included the first 8 hour of electrolyte spray exposure comprising repeated sequences consisting of half hour exposure to electrolyte spray followed by one and half hours of a rest period. The electrolyte used was a mixture of 0.9% NaCl, 0.1% $CaCl_2$ and 0.25% $NaHCO_3$, all in weight percentage based on the total weight. The foregoing eight hour electrolyte spray exposure was followed by 8.0 hour humidity exposure at 50° C. and 100% RH and then 8.0 hour exposure at 60° C. in oven. Duplicate coupons for each of the E-coating systems were used in the test. Each coupon after the aforedescribed conventional corrosion test was subjected to creep test using a conventional creep measurement device and the creep in millimeters was reported. The creep data were then transferred into the corrosion resistance by using the following equation:

Equivalent corrosion resistance (ohm)=B/Creep=300000/Creep wherein B is a transformation factor in ohm/mm, which can be affected by the kind of metal substrate used and the aggressiveness of the corrosion testing method. The data transformation was necessary for the purpose of comparison since the data obtained by the corrosion resistance evaluator of the present invention were in the form of corrosion resistance.

Corrosion Data from the Corrosion Test Method of the Present Invention:

Eight E-coating systems designated as coating A, B, C, D, F, G, H and I were applied on coupons and cured. On the coated surfaces of such coupons, six holes with a diameter of 300 microns were drilled to provide standardized anode and cathode defect, respectively. Each of the holes penetrated through the thickness of the coating and stopped at the interface of metal/coating. Standardized anode and cathode defects were identical.

The corrosion test evaluator was based on a 26 hour test protocol that included 5 sets of AC impedance measurements during 12 hours of start-up period (DC Volts=0), followed by four preset durations, each duration lasting two hours at stepped voltages starting from 0.5 Volts, followed by 1 Volt, 2 Volts, and 3 Volts. One set of AC impedance measurement was performed at the end of each preset duration. A 1.5 hour of recovery period was used in between each preset duration. One set of AC impedance measurement was made at the end of each recovery period. The corrosion performance resistance of the coating was calculated by using the following equation:

$$R_{perf}=[\Sigma^{Sta}f_{n1}(^{Sta}R_{Sta.n1}-^{Sta}R_{Sol.n1})]/n1+[\Sigma^{Stp}f_{n2}(^{Stp}R_{Sol.n2}-^{Stp}R_{Sol.n2})]/n2+[\Sigma^{Rec}f_{n3}(^{Rec}R_{Rec.n3}-^{Rec}R_{Sol.n3})]/n3,$$

wherein n1 is 5, n2 is 4, and n3 is 4 and $^{Sta}f_{n1}$, $^{Rec}f_{n2}$, and $^{Rec}f_{n3}$ are all equal to 1.

The foregoing $^{Sta}R_{Sta.n1}$, $^{Stp}R_{Stp.n2}$, and $^{Rec}R_{Rec.n3}$ determined by the real part of the ac impedance at $10^{-2}$ Hz from each of the respective ac impedance measurements obtained in the respective periods. $^{Sta}R_{Sol.n1}$, $^{Stp}R_{Sol.n2}$, and $^{Rec}R_{Sol.n3}$ were determined by the real part of the ac impedance at 100000 Hz from each of the respective ac impedance measurements obtained in the respective periods. The following provides further explanation of various element used in measuring the foregoing elements:

A typical ac impedance data (for coating H) obtained by the method of this invention can be described in FIG. 10. The impedance data was obtained using a frequency scan from 100000 Hz to $10^{-2}$ Hz. This plot is called Nyquist plot with a minus imaginary part as Y axis and a real part as X axis. The shortcoming of this plot is that the frequency is not explicitly expressed in the plot. Since the impedance, as noted earlier, is frequency dependent, the impedance is changed when the frequency is changed. By the impedance data at various frequencies (normally from 100000 Hz to $10^{-2}$ Hz), the resistance component and capacitance component can be separated and obtained respectively. For example, on the far left hand of FIG. 10 which is expanded as FIG. 12, a solution resistance in the start up period, $^{Sta}R_{Sol.2}$, can be obtained by selecting the real part of the impedance at 100000 Hz. On the far right hand of FIG. 10, which is expanded as FIG. 13, a start up resistance $^{Sta}R_{Sta.2}$ can be obtained by selecting the real part of the impedance at $10^{-2}$ Hz. The value of ($^{Sta}R_{Sta.2}$–$^{Sta}R_{Sol.2}$) is also showed in FIG. 10, which can be used to calculate the corrosion resistance of the coating tested.

Figure 14:
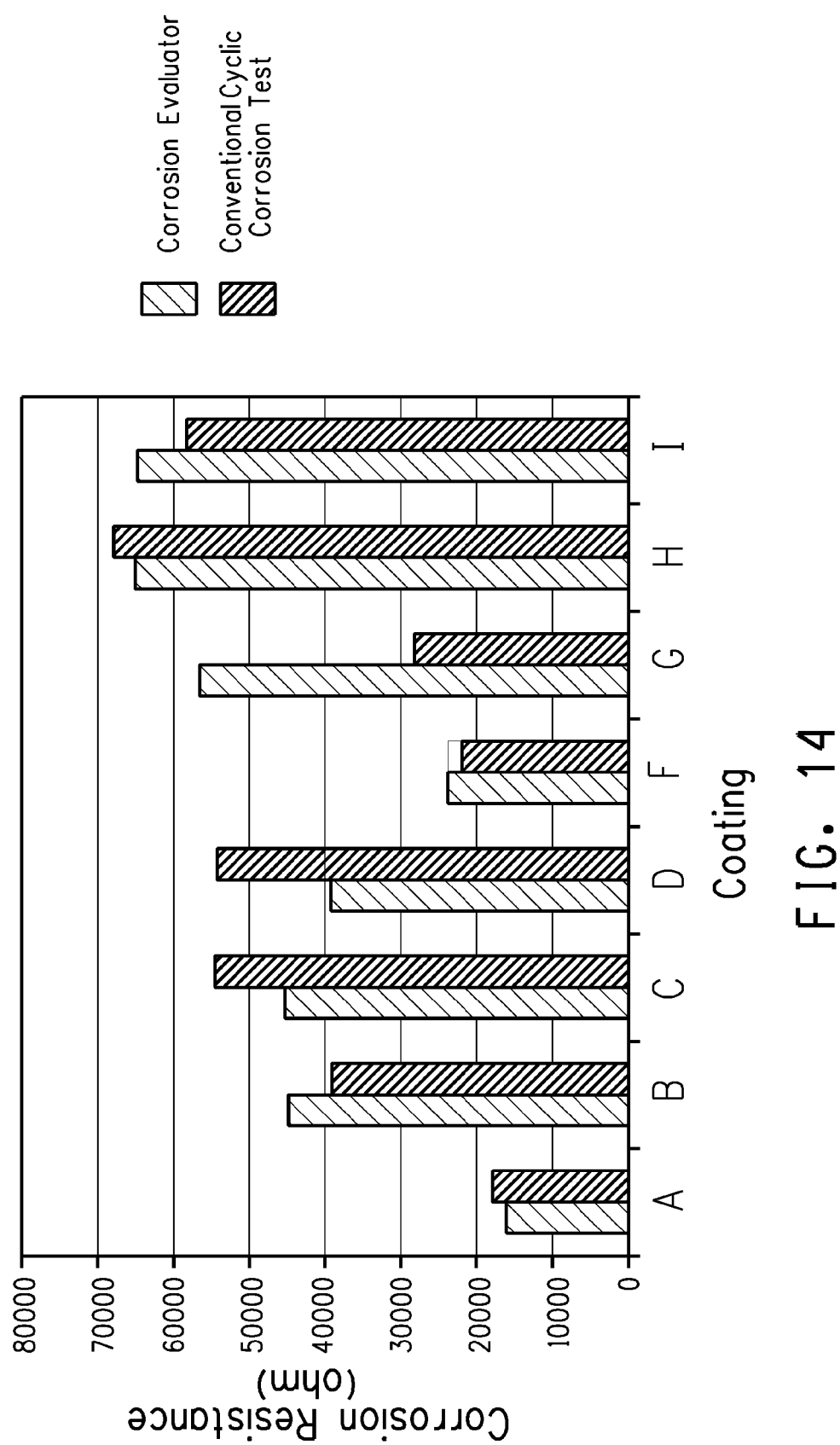
FIG. 14 illustrates the correlation and comparison of the results obtained by using the corrosion evaluation process of current invention against those obtained by using a well known conventional cyclic corrosion evaluation test.

The corrosion resistance data obtained by the corrosion evaluator of the present invention and a conventional cyclic corrosion test is shown in FIG. 14. From FIG. 14, one can readily observe that there was substantial correlation between the conventional corrosion test method and the corrosion test method of the present invention. The correlation coefficient of these two methods can be calculated by using the conventional definition of Pearson product-moment correlation coefficient. The Pearson product-moment correlation coefficient is a well-known correlation coefficient indicating the strength and direction of a linear relationship between two random variables. The correlation coefficient of these two methods was 74%, which is very high compared to the correlation coefficient between any other two conventional coating evaluation methods, which is less than 55%. Therefore, the accelerated corrosion resistance evaluator correlates very well with the conventional corrosion test method.

The discrepancy observed in the coating evaluation tests is primarily due to the difficulty in preparing the coated samples with the exactly same quality and the subjective nature of the evaluation methods used in the conventional corrosion tests.

The discrepancy observed on E-coating G can be explained in the following manner:

For the same E coating formulation, the pretreatments should be ranked from the best to the poorest as Zn phosphate>iron phosphate>none. This ranking is well known based on the prior experience and the knowledge of corrosion science. It was shown from FIG. 14 that both methods can correctly identify this ranking (compare coating A, B, and C in one group and compare coating F, G, and H in the second group). Also from FIG. 14 and Table 1 below, it can be seen that most of the data showed that for the same pretreatment, E-coating 2 performs better than E-coating 1 (compare coating F to coating A, coating G to coating B, coating H to coating C, and coating I to coating D). The corrosion evaluation method of the present invention identified such a trend with 100% accuracy while the conventional cyclic corrosion methods identify this trend with only one exception of coating G. Therefore, it is highly likely that the data of the coating G obtained by the method of the present invention is more accurate and more trustable.

TABLE 1

E-coated coupons for the correlation test

| Label | Pretreatment | E-coating | Bake Time and Temperature |
|---|---|---|---|
| A | None | E-coating 1 | 10 minutes at 360° F. |
| B | Iron phosphate | E-coating 1 | 10 minutes at 360° F. |
| C | Zn phosphate | E-coating 1 | 10 minutes at 360° F. |
| D | Zn phosphate | E-coating 1 | 18 minutes at 310° F. |
| E | None | E-coating 2 | 10 minutes at 360° F. |
| G | Iron phosphate | E-coating 2 | 10 minutes at 360° F. |
| H | Zn phosphate | E-coating 2 | "10 minutes at 360° F. |
| I | Zn phosphate | E-coating 2 | 18 minutes at 310° F. |

What is claimed is:

1. A process for evaluating corrosion resistance of an anode coating applied over a surface of an anode and corrosion resistance of a cathode coating applied over a surface of a cathode comprising:
   (i) sealably positioning said anode in an anode holder located on a chamber of a corrosion resistance evaluator, said chamber containing an electrolyte therein such that a portion of said anode coating is exposed to said electrolyte, said portion of said anode coating having an anode defect thereon;
   (ii) sealably positioning said cathode in a cathode holder located on said chamber such that a portion of said cathode coating is exposed to said electrolyte, said portion of said cathode coating having a cathode defect thereon;
   (iii) directing a computer of said evaluator through computer readable program code means residing on a usable storage medium located in said computer and configured to cause said computer to perform following steps comprising:
   a) subjecting said portions of said anode coating and said cathode coating to a start-up period;
   b) directing an impedance measurement device in communication with said computer and is connected to said cathode and said anode to measure an impedance A across the cathode and anode during said start-up period at preset intervals to produce n1 set of said impedances A measured at preset frequencies ranging from 100000 to $10^{-6}$ Hz of AC power with an amplitude ranging from 10 to 50 mV supplied by an alternating current variable power generator in communication with said computer, said alternating current variable power generator having AC output leads that connect to said cathode and anode;
   c) generating A impedance Nyquist plot for each said impedance A in said n1 set;
   d) determining start-up solution resistances ($^{Sta}R_{sol.n1}$) by:
      1. measuring a distance between zero point on X-axis of said A impedance Nyquist plot and a point on said X-axis of said A impedance Nyquist plot where an impedance curve or an extrapolated impedance curve directed to high start-up solution frequencies in said A impedance Nyquist plot intersects said X-axis to obtain real part of said impedance A at said high start-up solution frequencies; and
      2. repeating said step (d) (1) for each said impedance A in said n1 set;
   e) determining start-up resistances ($^{Sta}R_{Sta.n1}$) by:
      1. measuring a distance between zero point on X-axis of said A impedance Nyquist plot and a point on said X-axis of said A impedance Nyquist plot where an impedance curve or an extrapolated impedance curve directed to low start-up resistance frequencies in said A impedance Nyquist plot intersects said X-axis to obtain real part of said impedance A at said low start-up resistance frequencies; and
      2. repeating said step (e) (1) for each said impedance A in said n1 set;
   f) directing a direct current variable power generator to apply V1 preset DC voltages in a stepwise manner for T1 preset durations, wherein said direct current measurement device in communication with said computer and connected to said cathode and said anode is used to measure said preset DC voltages and wherein said V1 preset DC voltage ranges from 0.1 millivolts to 10 volts and said T1 preset duration ranges from half an hour to 100 hours;
   g) directing said impedance measurement device to measure an impedance B at the end of each of said preset duration at said preset frequencies of AC power supplied by said alternating current variable power generator to produce n2 set of said impedances B;

19 h) generating B impedance Nyquist plot for each said impedance B in said n2 set;
i) determining stepped-up solution resistances ($^{Stp}R_{sol.n2}$) by:
   1. measuring a distance between zero point on X-axis of said B impedance Nyquist plot and a point on said X-axis of said B impedance Nyquist plot where an impedance curve or an extrapolated impedance curve directed to high stepped-up solution frequencies in said B impedance Nyquist plot intersects said X-axis to obtain real part of said impedance B at said high stepped-up solution frequencies;
   2. repeating said step (i) (1) for each said impedance B in said n2 set;
j) determining stepped-up resistances ($^{Stp}R_{Stp.n2}$) by:
   1. measuring a distance between zero point on X-axis of said B impedance Nyquist plot and a point on said X-axis of said B impedance Nyquist plot where an impedance curve or an extrapolated impedance curve directed to low stepped-up resistance frequencies in said B impedance Nyquist plot intersects said X-axis to obtain real part of said impedance B at said low stepped-up resistance frequencies; and
   2. repeating said step (j) (1) for each said impedance B in said n2 set;
k) subjecting said portions of said anode coating and said cathode coating to T2 preset recovery periods in between each of said T1 preset durations;
l) directing said impedance measurement device to measure an impedance C at the end of each of said T2 preset recovery periods at said preset frequencies of AC power supplied by said alternating current variable power generator to produce n3 set of said impedances C;
m) generating C impedance Nyquist plot for each said impedance C in said n3 set;
n) determining recovery solution resistances ($^{Rec}R_{sol.n3}$) by:
   1. measuring a distance between zero point on X-axis of said C impedance Nyquist plot and a point on said X-axis of said C impedance Nyquist plot where an impedance curve or an extrapolated impedance curve directed to high recovery solution frequencies in said C impedance Nyquist plot intersects said X-axis to obtain real part of said impedance C at said high recovery solution frequencies;
   2. repeating said step (n) (1) for each said impedance C in said n3 set;
o) determining recovery resistances ($^{Rec}R_{Rec.n3}$) by
   1. measuring a distance between zero point on X-axis of said C impedance Nyquist plot and a point on said X-axis of said C impedance Nyquist plot where an impedance curve or an extrapolated impedance curve directed to low recovery resistance frequencies in said C impedance Nyquist plot intersects said X-axis to obtain real part of said impedance C at said low recovery resistance frequencies; and
   2. repeating said step (o) (1) for each said impedance C in said n3 set;
p) calculating corrosion performance resistance ($R_{perf}$) of said anode and said cathode pair by using the following equation:

$$R_{perf} = [\Sigma^{Sta}f_{n1}](^{Sta}R_{Sta.n1} - {}^{Sta}R_{Sol.n1})]/n1 + [\Sigma^{Stp}f_{n2}({}^{Stp}R_{Stp.n2} - {}^{Stp}R_{Sol.n2})]/n2 + [\Sigma^{Rec}f_{n3}({}^{Rec}R_{Rec.n3} - {}^{Rec}R_{Sol.n3})]/n3,$$

20 wherein n1, n2, and n3 are constant values that range from 1 to 100; and $^{Sta}f_{n1}$, $^{Stp}f_{n2}$, and $^{Rec}f_{n3}$ are constant values that range from 0.0000001 to 1, and wherein the constant value for n1, n2, and n3 is the number of values that are summed for each summation; and q) causing computer to direct a computer monitor to:
   (q1) display the corrosion performance resistance ($R_{perf}$),
   (q2) direct a printer to print the corrosion performance resistance ($R_{perf}$),
   (q3) transfer the corrosion performance resistance ($R_{perf}$) to a remote computer or a remote database, or
   (q4) a combination thereof.

2. The process of claim 1 wherein said cathode and said anode are made of steel.

3. The process of claim 1 wherein said anode coating and said cathode coating results from a multilayer coating composition comprising an automotive OEM paint, an automotive refinish paint, a marine paint, an aircraft paint, an architectural paint, an industrial paint, a rubberized coating, a polytetrafluoroethylene coating, or a zinc-rich primer.

4. The process of claim 1 wherein said chamber is surrounded by a thermal jacket to maintain temperature of said electrolyte at a desired temperature ranging from 0.5° C. to 99.5° C.

5. The process of claim 1 wherein two or more of said chambers are surrounded by a thermal jacket to maintain temperature of said electrolyte in each of said chambers at a desired temperature ranging from 0.5° C. to 99.5° C.

6. The process of claim 1 wherein said anode coating is identical to said cathode coating.

7. The process of claim 1 or 6 wherein said anode defect is identical to said cathode defect.

8. The process of claim 1 or 6 wherein said anode defect comprises a plurality of circular openings disposed on said coating that expose said underlying surface of said anode to said electrolyte.

9. The process of claim 1 or 6 wherein said cathode defect comprises a plurality of circular openings disposed on said coating that expose said underlying surface of said cathode to said electrolyte.

10. The process of claim 9 wherein said cathode or anode defect comprises circular openings each having a diameter in the range of from 5 micrometers to 5 millimeters, each said circular opening being uniformly separated from one another by 10 to 1000 times the diameter of said circular openings.

11. The process of claim 10 wherein said cathode or anode defect comprises in the range of from 1 to 100 of said circular openings per square centimeter of said cathode or anode, said circular opening being uniformly separated from one another, and wherein said circular opening has a diameter in the range of from 5 micrometers to 5 millimeters, each said circular opening being uniformly separated from one another by 10 to 2000 times the diameter of said circular openings.

12. The process of claim 10 wherein said cathode or anode defect comprises in the range of from 1 to 100 of said circular openings per square centimeter of said cathode or anode, said circular opening being uniformly separated from one another, and wherein said circular opening has a diameter in the range of from 5 micrometers to 3 millimeters.

13. The process of claim 1 wherein said electrolyte comprises:
   (a) an aqueous solution containing sodium chloride at a concentration of 3 parts by weight based on 100 parts by weight of said aqueous solution, (b) an aqueous solution that simulates acid rain, or (c) a corrosive chemical solution.

14. The process of claim 1 wherein said chamber comprises an inverted 'Y' shape, and wherein said anode holder and said cathode holder are each located on a leg of said inverted 'Y' to permit any gas generated during use or gas bubbles adhered on the surface of coated coupons during installation to escape readily from said chamber.

15. The process of claim 1 wherein said anode holder and said cathode holder are positioned at the opposite ends of said chamber to permit any gas generated during use to escape readily from said chamber.

16. The process of claim 1 wherein said start-up period ranges from half an hour to one thousand hours.

17. The corrosion resistance evaluator of claim 1 wherein said preset interval ranges from half an hour to ten hours.

* * * * *